(12) United States Patent
Miller

(10) Patent No.: US 8,679,776 B2
(45) Date of Patent: Mar. 25, 2014

(54) ACTIVATABLE DYES

(75) Inventor: Stephen C. Miller, Cambridge, MA (US)

(73) Assignee: University of Massachusetts, Boston, MA (US)

( * ) Notice: Subject to any disclaimer, the term of this patent is extended or adjusted under 35 U.S.C. 154(b) by 649 days.

(21) Appl. No.: 12/677,962

(22) PCT Filed: Sep. 12, 2008

(86) PCT No.: PCT/US2008/076268
§ 371 (c)(1),
(2), (4) Date: Jul. 26, 2010

(87) PCT Pub. No.: WO2009/036351
PCT Pub. Date: Mar. 19, 2009

(65) Prior Publication Data
US 2010/0297684 A1 Nov. 25, 2010

Related U.S. Application Data

(60) Provisional application No. 60/972,065, filed on Sep. 13, 2007.

(51) Int. Cl.
*C12Q 1/02* (2006.01)
*C07D 265/38* (2006.01)
*C07D 498/00* (2006.01)
*C07D 295/00* (2006.01)

(52) U.S. Cl.
USPC .................. 435/29; 544/75; 544/99; 544/103

(58) Field of Classification Search
USPC ................................. 435/29; 544/75, 99, 103
See application file for complete search history.

(56) References Cited

U.S. PATENT DOCUMENTS

| 4,139,390 | A | 2/1979 | Rauner et al. |
| 4,857,438 | A | 8/1989 | Loerzer et al. |
| 5,389,489 | A | 2/1995 | Yanagihara et al. |
| 6,194,223 | B1 * | 2/2001 | Herrmann et al. ............ 436/518 |
| 2008/0233609 | A1 | 9/2008 | Miller et al. |
| 2008/0299592 | A1 | 12/2008 | Miller |

OTHER PUBLICATIONS

STN abstract for US 6,194,223 downloaded from file CAPLUS Jul. 22, 2012.*
Creed et al. JCS Comm (1981) 10: 497-499.*
Machine translation of JP 2005-320502 downloaded from the JPO Sep. 12, 2012.*
Akiba et al. Proc. of SPIE Linear and Nonlinear Optics of Orgnaic Materials VI 6331 (Sep. 14, 2006) pp. 633010F-1 to 633010F-10.*
Hintersteiner et al. Nature Biotechology (2005) 23(5): 577-583.*
Ando et at., "An optical marker based on the UV-induced green-to-red photoconversion of a fluorescent protein," Proc. Natl. Acad. Sci. U.S.A., 99:12651-12656 (2002).
Cadierno et al., "Ru(IV)-catalyzed isomerization of allylamines in water: A highly efficient procedure for the deprotection of N-allylic amines," Chem. Commun., 4086-4088 (2005).
Furuta et al., "Brominated 7-hydroxycoumarin-4-ylmethyls: novel photolabile protecting groups with biological useful cross-sections for two photon photolysis," Proc. Natl. Acad. Sci. USA, 96:1193-1200 (1999).
International Preliminary Report on Patentability, PCT Serial No.: PCT/US2008/076268, dated Mar. 16, 2010.
International Search Report, PCT Serial No.: PCT/US2008/076268, dated Apr. 3, 2009.
Momotake et al., "The nitrodibenzofuran chromophore: a new caging group for ultra-efficient photolysis in living cells," Nature Methods, 3:35-40 (2006).
Wiedenmann et al., "EosFP, a fluorescent marker protein with UV-inducible green-to-red fluorescence conversion," Proc. Natl. Acad. Sci. U.S.A., 101:15905-15910 (2004).

* cited by examiner

*Primary Examiner* — Susan Hanley
(74) *Attorney, Agent, or Firm* — Fish & Richardson P.C.

(57) ABSTRACT

Novel, activatable dyes, such as photoactivatable dyes, e.g., oxazine dyes, are described. Some of the dyes are targeting dyes that can, e.g., target biomolecules, such as polypeptides, proteins, or nucleic acids. Upon activation, such as by irradiation, the novel dyes rapidly turn on their fluorescence and emit light, such as near-IR light with spatial and temporal precision.

11 Claims, 24 Drawing Sheets

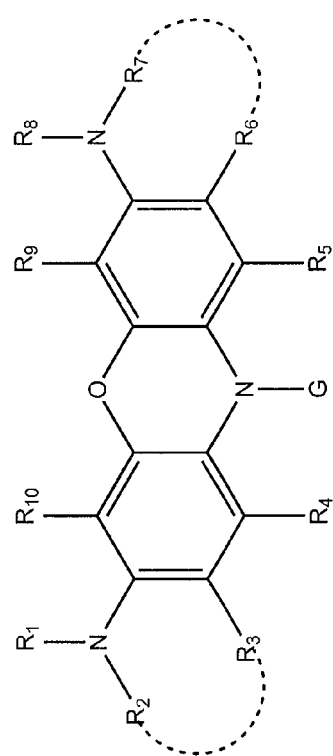
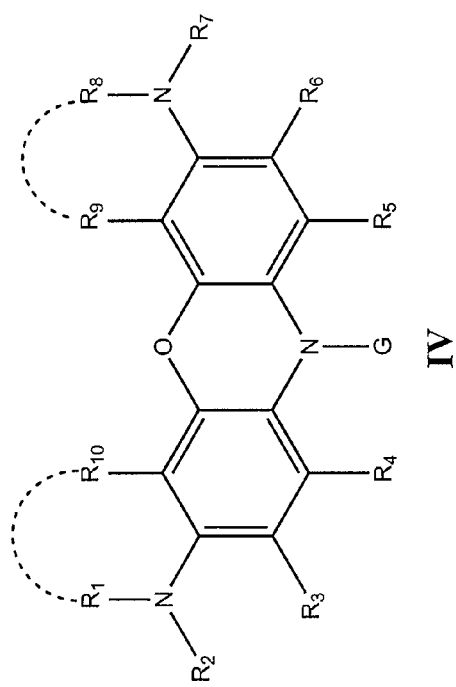
FIG. 2

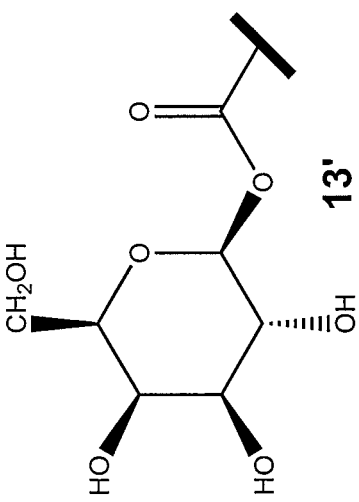
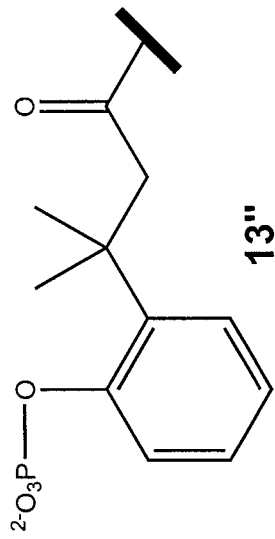
FIG. 5B
G can also be an enzymatically-labile group, such as
Beta-galactosidase substrates
Phosphatase substrate with trimethyl lock

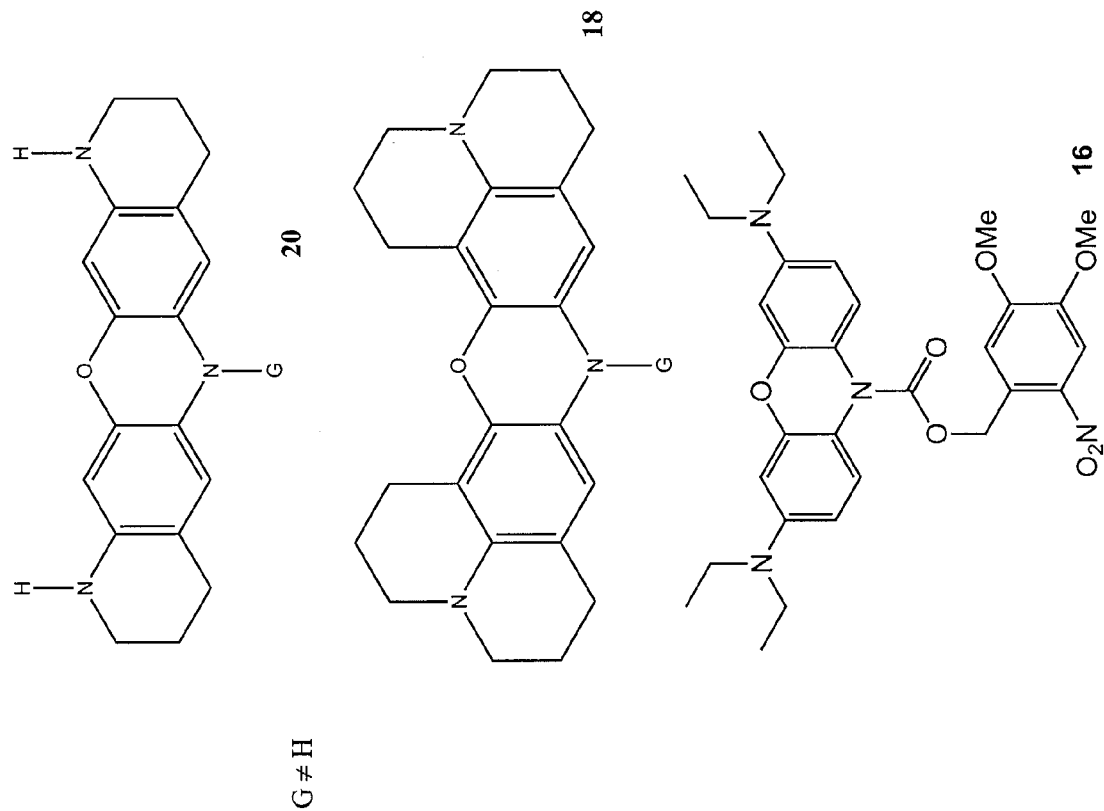

a) 3-chloropropionylchloride, NaHCO$_3$, TBAB, H$_2$O; b) AlCl$_3$, 140 °C; c) BH$_3$.Me$_2$S, 100 °C, Toluene; d) Allyl bromide/ Ethyl 3-bromopropionate, NaHCO$_3$, TBAB, H$_2$O; e) ArN$_2^+$BF$_4^-$, c.H$_2$SO$_4$; f) 21a-21c, EtOH, H$_2$O, HCl, 80 °C; g) Na$_2$S$_2$O$_4$, Toluene-Water-Methanol, NaHCO$_3$, NVOC-Cl; h) 29a, 2.5M HCl, acetone, 75 °C; i) N-hydroxysuccinimide, DIC, CH$_2$Cl$_2$-DMF, 50 °C; j) aminodextran, 0.1M NaHCO$_3$ a) bis(allyl) Ru(IV) complex, water, 100°C; b) NVOC-Cl, NaHCO₃, H₂O-CH₃CN; c) acetone, water, HCl, reflux; then NHS, DIC, DCM.

a) Chloroacetyl chloride, NaHCO₃, TBAB, H₂O; b) BBr₃, DCM, 0-4C; c) NaH, THF; d) BH₃-THF; e) K₂CO₃, DMF, EtBr (X) or ethyl 3-bromopropionate (Y); f) 4NO₂PhN₂+BF₄-, H₂SO₄, MeOH; g) HCl, EtOH, 75C; h) Na₂S₂O₄, toluene, water, NaHCO₃, NVOC-Cl; i) HCl, acetone, water, reflux; j) NHS, DIC, DCM.

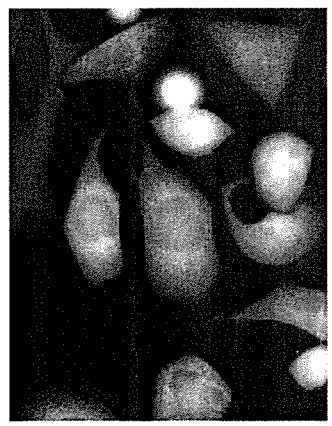
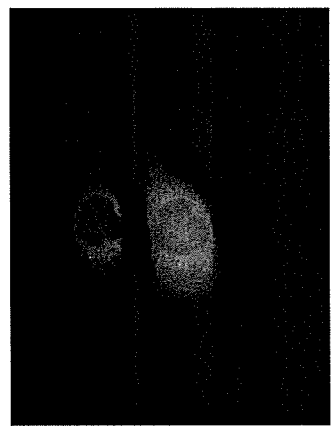
FIG. 21

US 8,679,776 B2

ACTIVATABLE DYES

CROSS-REFERENCE TO RELATED APPLICATIONS

This application is the national phase application under 35 U.S.C. §371 of PCT International Application No. PCT/US2008/076268, filed Sep. 12, 2008, which claims the benefit under 35 USC §119(e) of U.S. Provisional Patent Application Ser. No. 60/972,065, filed on Sep. 13, 2007; the entire contents of these applications are incorporated herein by reference.

TECHNICAL FIELD

This invention relates to activatable dyes, such as photoactivatable dyes, related compounds, and to uses of the same.

BACKGROUND

Photoactivation of fluorescence is a powerful technique for the study of biological molecules in living cells. In particular, this method allows the study of dynamic cellular processes by providing a means to make fiducial marks on biopolymers, monitor biomolecule diffusion, trace cell lineage, and differentiate between two or more populations of a biomolecule (e.g., newly synthesized proteins vs. older proteins, or nucleic acids). Examples of photoactivatable fluorophores include caged fluorescein and photoactivatable green fluorescent protein (PA-GFP). More recently, the use of photochromic proteins such as Kaede (Ando et al., Proc. Natl. Acad. Sci. U.S.A., 99:12651-12656 (2002)) have allowed the discrimination between two different populations of a biomolecule by a shift in the fluorescence emission wavelength after photo-activation.

Photoactivation of PA-GFP can be used to temporally mark a protein population, but it is restricted to green fluorescence. The photoconvertable proteins, Kaede and EOS, (Wiedenmann et al., Proc. Natl. Acad. Sci. U.S.A. 101:15905-15910 (2004)) shift their fluorescence from green to red upon irradiation with long-wave UV light. However, Kaede is an obligate tetramer, and EOS monomer fusion constructs do not express at physiological temperatures. Thus, these proteins can not currently be used in a general method to tag proteins of interest and mark their localization in cells. None of these fluorescent proteins efficiently emit light in the near-IR (>650 nm), where autofluorescence is lowest and light penetration through living tissue is highest. In addition, all of these proteins are relatively large in size (27 kD for the Kaede monomer) and can interfere with the proper localization and function of the protein under study.

Photoactivation of small molecule fluorophores has thus far been mostly limited to o-nitrobenzyl (oNB)-based caged derivatives of coumarin, fluorescein, Q-rhodamine, and resorufin. In these dyes, fluorescence in the caged dye is reduced by either i) alkylation of a free phenolic hydroxyl in the parent dye with an oNB derivative (e.g., present in coumarin, fluorescein and resorufin) or, ii) carbamoylation of a secondary aryl amine with an oNB derivative (e.g., in Q-rhodamine). Photocleavage of the oNB moiety restores the structure of the parent dye, resulting in a large increase in fluorescence. Many exemplary fluorophores either lack suitable free phenol or aryl amine functionality, or such modified derivatives are still fluorescent, and thus are not amenable to the chemical modifications required to render them photoactivatable using this approach. For example, longer-wavelength far-red and near-IR rhodamine and oxazine dyes that have tertiary aryl amines are not compatible with this approach.

While caged-fluorescein is the most widely-used photoactivatable fluorophore, it is highly hydrophobic, poorly soluble in water, and labeled protein tends to aggregate. Moreover, its synthesis is difficult and the fluorescein chromophore bleaches very rapidly. Photocaged coumarin is photoactivated at the same wavelength used to visualize coumarin fluorescence, which greatly limits its use. Photocaged Q-rhodamine is difficult to synthesize and uncages slowly, and caged resorufin is chemically unstable in cell extract. Furthermore, both caged fluorescein and caged Q-rhodamine have two photolabile groups each. Thus, restoration of full fluorescence is a stepwise process, as it requires the removal of both groups, and leads to a heterogeneous population of fluorescent molecules.

SUMMARY

Described herein are novel, activatable dyes, such as photoactivatable dyes, e.g., oxazine dyes, which have latent near-IR fluorophores. Some of the dyes are targeting dyes that can, e.g., target biomolecules, such as polypeptides, proteins, or nucleic acids. The novel molecules, and the methods described herein, allow compositions that contain the latent fluorophore to be activated, such as by irradiation, e.g., with long-wave UV light (e.g., light having a wavelength of about 360 nm); to rapidly turn on the fluorescence of a near-IR dye with spatial and temporal precision.

In one aspect, the invention features caged dyes that include a non-fluorescent core having a photolabile group covalently bonded thereto, such that upon irradiating the caged dyes with electromagnetic radiation having a wavelength of from about 325 nm to about 750 nm, the photolabile group is removed. For example, the excitation range can be from about 350 nm to about 420 nm for single photon excitation, or from about 650 nm to about 800 nm for two photon excitation. Upon removal of the photolabile group in the presence of an oxidizing agent, such as oxygen, the latent near-IR fluorophore is unmasked. For example, the resulting dye can have an oxazine core structure.

In another aspect, the invention features non-fluorescent caged dyes that are converted to fluorescent dyes that emit near-IR radiation when the caged dyes are irradiated with electromagnetic radiation having a wavelength of from about 325 nm to about 750 nm in the presence of an oxidant, such as oxygen. For example, the excitation range can be from about 350 nm to about 420 nm for single photon excitation, or from about 650 nm to about 800 nm for two photon excitation.

In some embodiments, the compounds after being irradiated with electromagnetic radiation having a wavelength from about 350 nm to about 405 nm, emit a fluorescence in the near-IR region.

In another aspect, the invention features caged dyes that include a non-fluorescent core having an enzymatically-labile group, e.g., a beta-galactosidase substrate, covalently bonded thereto, such that upon treatment with one or more enzymes, the enzymatically-labile group is removed. Upon removal of the enzymatically-labile group in the presence of an oxidizing agent, such as oxygen, a latent near-IR fluorophore is unmasked.

Embodiments and/or aspects described herein can have one or more of the following advantages. Some of the dyes (especially those in active cationic form) localize in specific organelles within cells, such as mitochondria, allowing for their imaging. This localization can allow for the study of various dynamic cellular processes. The photoactivatable dyes can be conjugated to various biomolecules, such as proteins, e.g., bearing one or more lysines, cysteines or tetracysteine tags, or nucleic acids. The photoactivatable dyes can also be conjugated with, e.g., hexahistidine tags, N-terminal cysteines or fusion tags, such as HaloTag, AGT (SNAP™tag), DHFR (DiHydroFolate Reductase) or FKBP (FK506 binding protein). Biomolecules, such as proteins or nucleic acids, can be labeled in living cells. The dyes, as synthesized in caged form, can be neutral and can be more cell permeable. The dyes can be stable to a variety of chemical environments, such as basic environments in which the pH is greater than 8.5. Only a single photocleavable group is required for photoactivation of the dyes, which can circumvent many of the structural limitations and step-wise photoactivation processes required by other methods, such as those imposed by the canonical bis-caging approach for fluorescein and Q-rhodamine. The dyes can be provided in labeling kits for various biomolecules, such as proteins or nucleic acids. Since fluorescence generally requires the presence of an oxidant, such as oxygen, the dyes can be used to detect the presence of such an oxidant. When conjugated to a moiety, such as a protein, that already includes a fluorophore, the dyes can modulate emission from the fluorophore. Thus, if a photoactivatable near-IR fluorophore was targeted to a green, yellow or red fluorescent protein or small molecule fluorophore, its uncaging, e.g., with long-wave UV light, could shift the emission wavelength by fluorescence resonance energy transfer (FRET) from the visible light donor to the photoactivated near-IR acceptor fluorophore. The novel dyes allow for greater control of the emission wavelengths, beyond those currently available. The dyes can have any selected emission and/or absorption by selection of the appropriate fluorophore. The fluorophore can absorb and/or emit in the infrared (IR), e.g., near-IR, or visible regions of the electromagnetic spectrum. Imaging in the near-IR can be advantageous since autofluorescence is minimal, and tissue penetration is the highest. The dyes can be relatively inexpensive to prepare. The targeting moiety can be selected independently of a payload (e.g., a fluorophore). The distance from the targeting moiety and the fluorophore can be pre-determined by selecting an appropriate tether. The novel dyes described herein may be used to image proteins and other biopolymers. Since these novel latent fluorophores are small relative to fluorescent proteins such as GFP, they are less likely to perturb cellular function and localization of a labeled protein.

As used herein, "a targeting moiety" is one that includes functionality that is electrophilic or nucleophilic in nature, allowing for conjugation to other moieties. For example, the targeting moiety can include a SplAsH residue, a chloroalkyl tether, a guanosine derivative, rapamycin, a trimethoprim derivative and a biotin derivative. The conjugation can be covalent or non-covalent. In some instances, the targeting moiety is reactive towards a nucleophile (the targeting moiety targets a nucleophile), such as an amino group or one or more thiol groups that form part of a target, such as a biomolecule, e.g., a protein or nucleic acid, and thus can be used to label the target biomolecule. Examples of functionalities that are reactive towards a nucleophile include NHS esters, maleimides, iodoacetamides, and bis-arsenicals (or their antimony analogs). The targeting moiety can also target a HaloTag™, His6 tags, AGT (SNAP™ tag), FKBP, DHFR, or avidin/streptavidin. A non-targeting moiety is one that does not contain the above reactive functionalities.

As used herein, a conjugate is a complex between a biomolecule, e.g., a peptide, protein, carbohydrate, oligonucleotide; and a dye, for example a photoactivatable dye.

All publications, patent applications, patents, and other references mentioned herein are incorporated by reference herein in their entirety for all that they contain.

Other features and advantages will be apparent from the following detailed description, and from the claims.

DESCRIPTION OF DRAWINGS

FIGS. 1-4 are a series of exemplary generalized structures for some novel dyes or functional groups on the dyes.

FIG. 5B is a series of two structures for possible enzymatically-labile groups.

FIG. 6 is a series of three structures for some specific non-targeting caged dyes.

FIG. 21 shows CHO-K1 tissue culture cells treated with a caged oxazine dye, before and after photoactivation. Photoactivation of NVOC-MR121 in live CHO-K1 cells before (a) and after (b, c) brief exposure to DAPI-filtered light (~100 ms). In (b) the field was limited to two cells, while in (c) the entire field was illuminated (40× objective). Cells were imaged with a Cy5 filter set.

DETAILED DESCRIPTION

Novel, activatable dyes, such as oxazine dyes, are described herein. Some of the dyes are targeting dyes that can, e.g., target or label biomolecules, such as polypeptides, proteins, and/or nucleic acids. These novel dyes, and the methods described herein, allow one to irradiate or enzymatically treat compositions that contain the dye to rapidly turn on the fluorescence of a near-IR dye. The dyes as synthesized are in caged or protected form, and thus are neutral (do not bear a charge) and can be more cell permeable. When conjugated to a moiety, such as a protein, that already includes a fluorophore, the dyes can modulate emission from the fluorophore after their uncaging. For example, a photoactivatable near-IR fluorophore targeted to a green, yellow, or red fluorescent protein or small molecule fluorophore can, after its uncaging, modulate the emission wavelength by fluorescence resonance energy transfer (FRET).

Caged and Leuco Dyes

Figure 1:
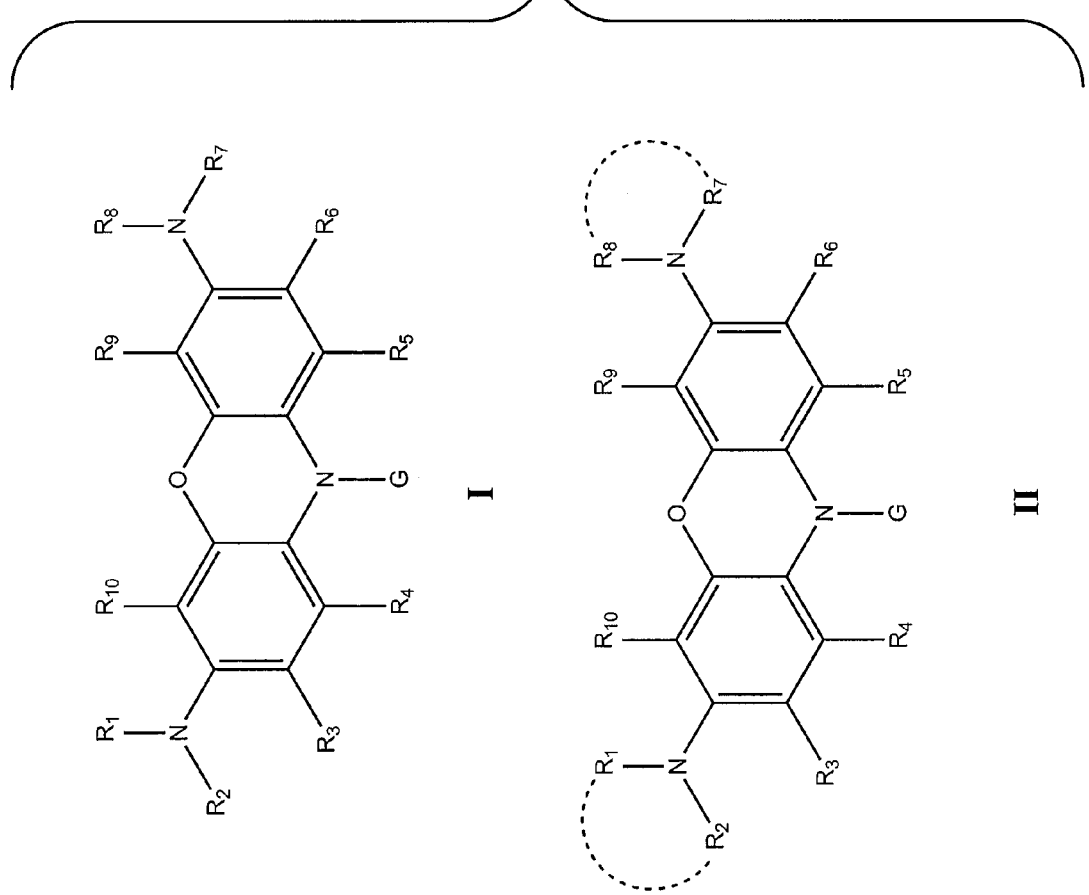

Generally, and by reference to FIG. 1, compounds of Structure (I) are provided. In such compounds, $R_1$, $R_2$, $R_7$ and $R_8$ are each independently H, a first non-targeting moiety that includes up to 36 carbon atoms, or a first targeting moiety that includes up to 36 carbon atoms; $R_3$, $R_4$, $R_5$, $R_6$, $R_9$ and $R_{10}$ are each independently H, F, Cl, Br, I, OH, or a second non-targeting moiety that includes up to 36 carbon atoms; any one or more of $R_1$, $R_2$, $R_3$ and $R_{10}$ together with one or more of its immediate neighbors and/or any one or more of $R_6$, $R_7$, $R_8$ and $R_9$ together with one or more of its immediate neighbors may define one or more ring systems, each ring system including up to 16 carbon atoms; and G is H, or a first non-targeting moiety that includes up to 24 carbon atoms. When G is a first non-targeting moiety that includes up to 24 carbon atoms, and G is removable from the compounds represented by Structure (I) when the compounds are either enzymatically treated or irradiated with electromagnetic radiation having a wavelength of from about 325 nm to about 750 nm, the dye with a Structure (I) is referred to herein as a caged or protected dye. The caged or protected dye (when G≠H) is not fluorescent, but can be converted to its, unprotected, leuco form (in which G is H), which in turn can be oxidized, e.g., by oxygen, to its corresponding fluorescent cationic form, referred to herein as active dye. The oxidation of the leuco form to the active dye (cationic) form will be discussed further below.

In some embodiments, the first and/or second non-targeting moiety/moieties that include/s up to 36 carbon atoms can also include, e.g., one or more N, O, P, S, F, Cl, Br, or I. For example, N can be part of an amino group or an amide group. For example, O can be part of hydroxyl group, an aldehyde group, a ketone group or an ether group. For example, S can be part of a thiol group. For example, P can be part of a phosphate group, a phosphonate group, a phosphine group, or a phosphoramide group.

In other embodiments, the first and/or second non-targeting moiety/moieties that include/s up to 36 carbon atoms is/are or include/s a hydrocarbon fragment, e.g., an alkyl group, an alkenyl group, an alkynyl or an aryl group, or a hydrocarbon fragment that is substituted with one or more of N, O, P, S, F, Cl, Br, or I.

In compounds of Structure (I), any one or more of $R_1$, $R_2$, $R_3$ and $R_{10}$ together with one or more of its immediate neighbors and/or any one or more of $R_6$, $R_7$, $R_8$ and $R_9$ together with one or more of its immediate neighbors may define one or more ring systems (e.g., 5- or 6-membered rings), each ring system including up to 16 carbon atoms. For example, the one or more rings can further include in a ring or substituted on the ring, e.g., one or more of N, O, P, S, F, Cl, Br, or I. For example, the balance of the 14 carbons atoms not in a ring can substitute a ring, e.g., in the form of hydrocarbon fragments, e.g., an alkyl group, an alkenyl group, an alkynyl or an aryl group, or a hydrocarbon fragment that is substituted with one or more of N, O, P, S, F, Cl, Br, or I. For example, N can be part of an amino group, or an amide group. For example, O can be part of hydroxyl group, an ester group, an aldehyde group, a ketone group or a ether group. For example, S can be part of a thiol group.

In some embodiments, $R_1$ and $R_2$ combine to form a ring, and $R_7$ and $R_8$ together combine to form a ring. In such instances, compounds of Structure (I) are represented by Structure (II), which is shown in FIG. 1.

In certain embodiments, $R_2$ and $R_3$ combine to form a ring, and $R_6$ and $R_7$ together combine to form a ring, or $R_1$ and $R_{10}$ combine to form a ring, and $R_8$ and $R_9$ together combine to form a ring. In such instances, compounds of Structure (I) are represented by Structures (III) and (IV), respectively, which are shown in FIG. 2.

Figure 3:
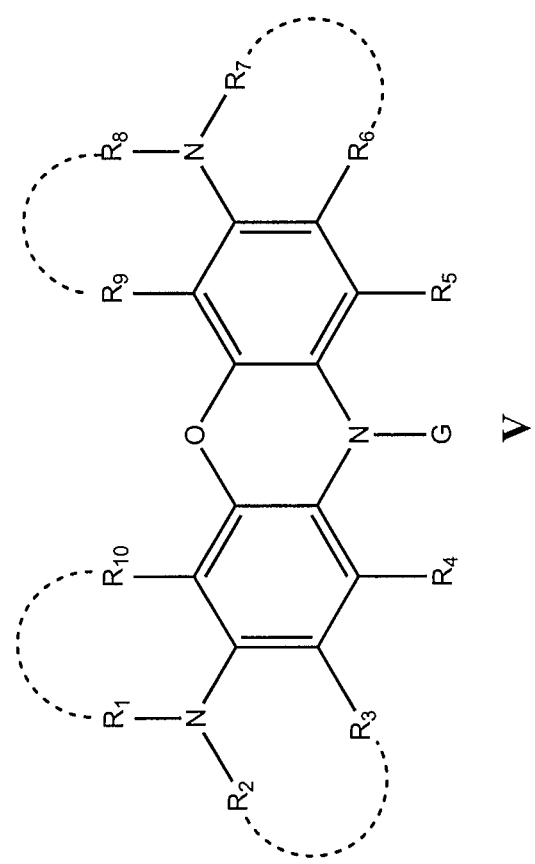

In still other embodiments, $R_1$ and $R_{10}$ combine to form a ring, $R_2$ and $R_3$ combine to form a ring, $R_6$ and $R_7$ combine to form a ring, and $R_8$ and $R_9$ combine to form a ring. In such instances, compounds of Structure (I) are represented by Structure (V), which is shown in FIG. 3.

In some embodiments, one or more of $R_1$, $R_2$, $R_7$ and $R_8$ is a first targeting moiety, allowing the dyes to be conjugated to various biomolecules, such as proteins, e.g., those bearing tetracysteine tags, or nucleic acids.

For example, in some embodiments, one or more of $R_1$, $R_2$, $R_7$ and $R_8$ is a first targeting moiety that includes one or more As or Sb atoms. For example, in some embodiments, the targeting moiety that includes a non-fluorescent bis-arsenical spirolactam targeting group, such as the bis-arsenical targeting group (12) shown in FIG. 4. Other bis-arsenical groups (and their antimony analogs) are described in SPIROLACTAM TARGETING COMPOUNDS AND RELATED COMPOUNDS, U.S. Provisional Patent Application Ser. 60/904,599, filed Mar. 2, 2007.

In certain embodiments, one of $R_1$, $R_2$, $R_7$ or $R_8$ is a first targeting moiety that includes an NHS ester group, a maleimide group, or an iodoacetamide group, allowing for easy conjugation, e.g., to a biomolecule such as a protein, e.g., bearing one or more amino groups and/or thiol groups, or a nucleic acid.

Figure 4:
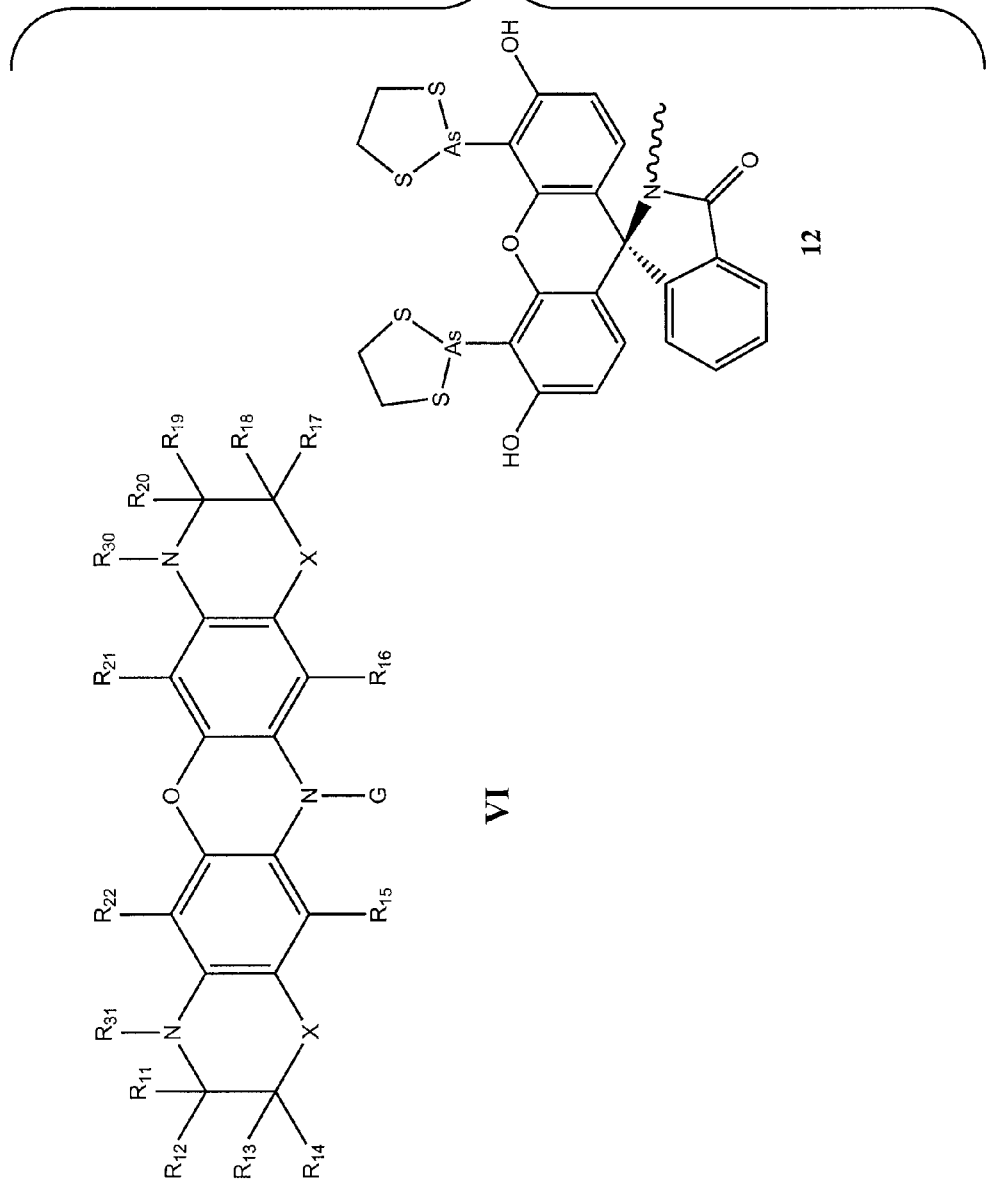

In certain embodiments, compounds of Structure (I) are represented by compounds of Structure (VI), which is shown in FIG. 4. In such embodiments, X is O, S, NH, or $CR^{23}R^{24}$; $R_{30}$ and $R_{31}$ are each independently H, a third non-targeting moiety that includes up to 36 carbon atoms, or a second targeting moiety that includes up to 36 carbon atoms; $R_{12}$-$R_{24}$ are each independently H, F, Cl, Br, I, OH, or a fourth non-targeting moiety that includes up to 36 carbon atoms; and G is H, or a second non-targeting moiety that includes up to 24 carbon atoms. As was the case with compounds of Structure (I), which were described above, when G is a second non-targeting moiety that includes up to 24 carbon atoms, G is removable from the compounds represented by Structure (VI) when the compounds are irradiated with electromagnetic radiation having a wavelength of from about 325 nm to about 750 nm, or in the alternative, by treatment with one or more enzymes.

The third non-targeting moiety and the fourth non-targeting can be any of those moieties described herein in reference to the first and second moieties including up to 36 carbon atoms. The second non-targeting moiety can be any of those described herein in reference to the first non-targeting moiety that includes that includes up to 24 carbon atoms. In addition, the second targeting moiety can be any of those moieties described in reference to the first targeting moiety comprising up to 36 carbon atoms.

As described, generally, when G is first non-targeting moiety that includes up to 24 carbon atoms, it can be removed from compounds of Structures (I) or (VI) when the compounds are irradiated with electromagnetic radiation having a wavelength of from about 325 nm to about 750 nm, or in the alternative, by treatment with enzymes. In addition to the 24 carbon atoms, G can also include, e.g., one or more N, O, P, S, F, Cl, Br, or I. For example, N can be part of an amino group or an amide group. For example, O can be part of hydroxyl group, an aldehyde group, a ketone group or an ether group. For example, S can be part of a thiol group. For example, P can be part of a phosphate group, a phosphonate group, a phosphine group, or a phosphoramide group.

Figure 5A:
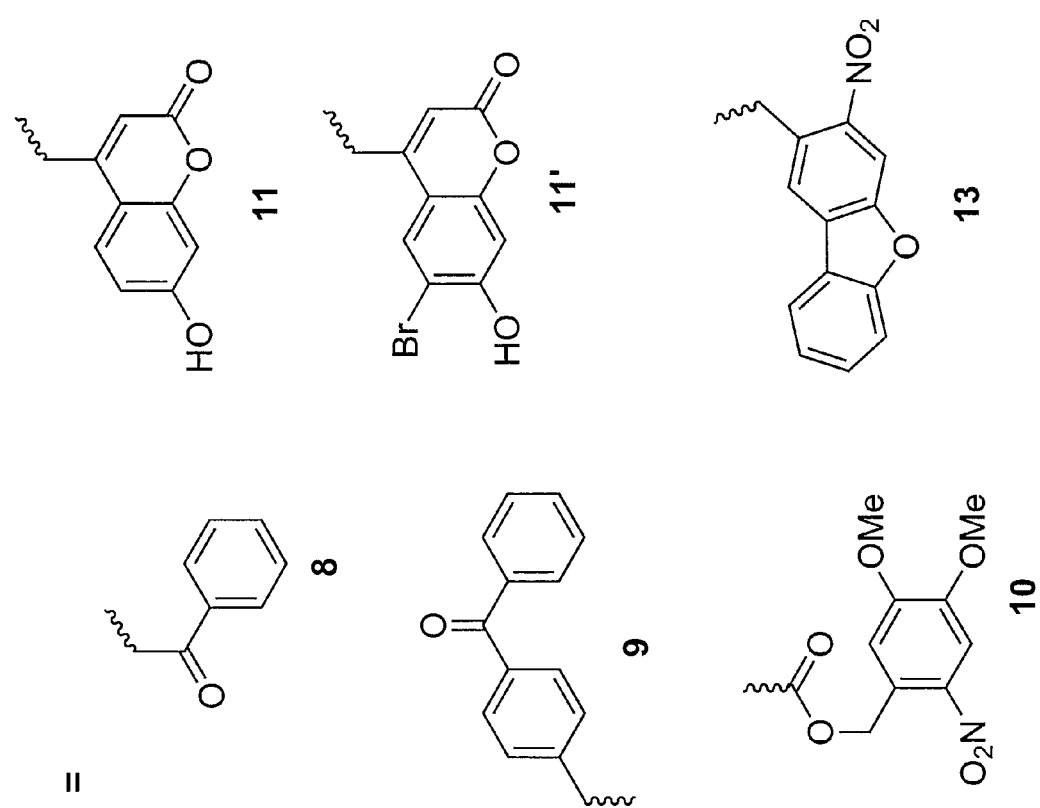
FIG. 5A is a series of six structures for several possible photolabile groups.

Specific examples of G are shown in FIG. 5A. For example, G can be a phenacyl group, which has a member represented by (8), a benzophenone group, which has a member represented by (9), a nitroveratryloxycarbonyl (NVOC) group, which is represented by (10), a coumarin group, which has a member represented by (11 or 11'), a nitrodibenzofuran group, which has a member represented by (13), or a carboxynitrobenzyl group (not shown). Various other examples of G are described in Furuta et al., Proc. Natl. Acad. Sci. USA, 96:1193-1200 (1999) and Momotake et al., Nature Methods, 3:35-40 (2006).

G can also be an enzymatically-labile group, such that upon treatment with one or more enzymes, the enzymatically-labile group is removed. Upon removal of the enzymatically-labile group in the presence of an oxidizing agent, such as oxygen, a latent near-IR fluorophore is unmasked. Specific examples of enzymatically-labile groups are shown in FIG. 5B. For example, the enzymatically-labile group can be a beta-galactosidase substrate, such as (13') or a phophatase substrate with trimethyl lock, such as (13").

Figure 7:
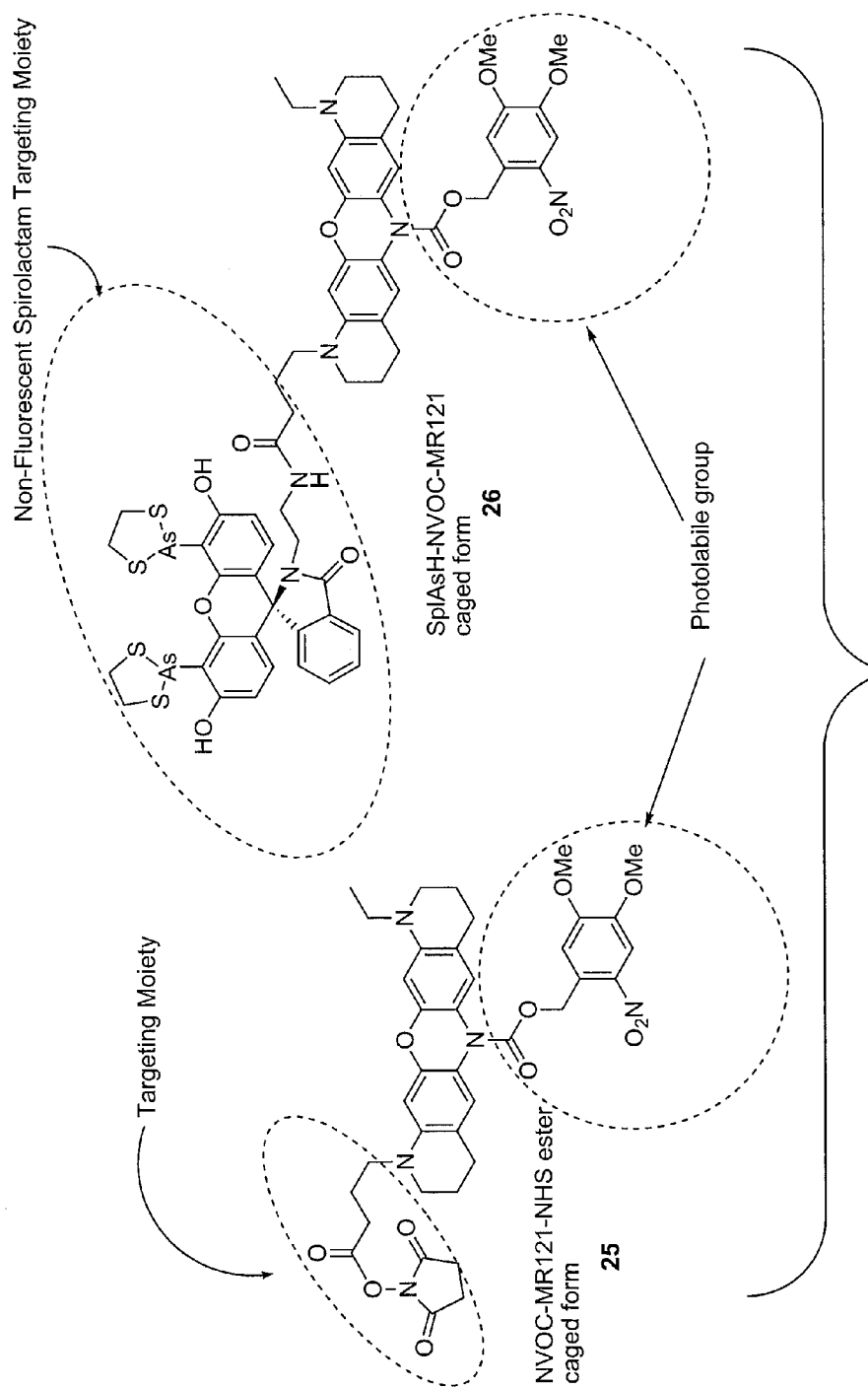
FIG. 7 is a pair of structures for several specific targeting caged dyes.

Specific examples of non-targeting caged dyes are shown in FIG. 6 ((16), (18) and (20)), while specific caged targeting dyes are shown in FIG. 7 ((25) and (26)). Compound (25, NVOC-MR121-NHS ester), is a non-florescent caged targeting dye that includes a photolabile NVOC group, and a targeting moiety that includes an active NHS ester, e.g., that can target an amino group of a protein. Compound (26, SplAsH-NVOC-MR121) is a non-florescent caged targeting dye that includes a photolabile NVOC group, and a non-fluorescent bis-arsenical spirolactam targeting moiety that include a bis-arsenical group that can, e.g., target a tetracysteine tagged protein. Tetracysteine tagged proteins are described in RED-SHIFTED LUCIFERASE, U.S. patent application Ser. No. 12/040,797, Filed Feb. 29, 2008; and SPIROLACTAM TARGETING COMPOUNDS AND RELATED COMPOUNDS, U.S. Provisional Patent Application Ser. 60/904,599, filed Mar. 2, 2007. Both compounds (25) and (26) can be conjugated to a biomolecule, and then irradiated, e.g., with UV light having a wavelength of about 360 nm, causing loss of the NVOC protecting group to generate the non-fluorescent leuco form of the dye conjugated to the protein, which is rapidly oxidized by oxygen to generate fluorescent protein.

Active Dyes

Figure 8:
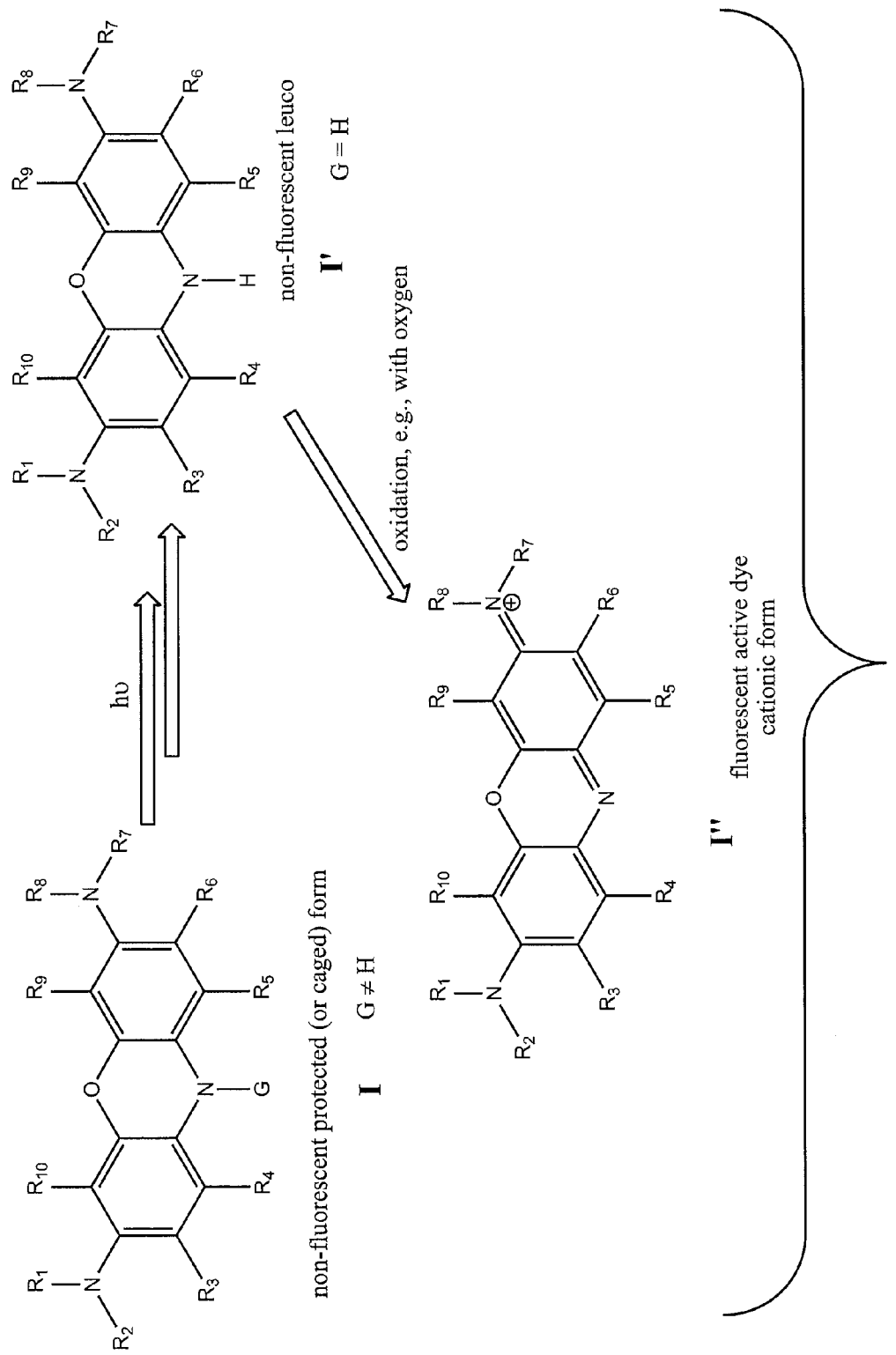
FIG. 8 is a series of three structures that illustrate conversion of a protected or caged dye into its leuco form, and then oxidation of the leuco dye to an active (fluorescent), cationic form.

Referring now to FIG. 8, a fluorescent active dye, represented by Structure (I"), is generated from a non-fluorescent caged dye (or a conjugate thereof), represented by Structure (I), by irradiating the caged dye (or conjugate) with electromagnetic radiation having a wavelength of from about 325 nm to about 750 nm or by treating with one or more enzymes. Irradiation or treatment with one or more enzymes causes loss the G from the caged dye to produce the non-fluorescent leuco form of the caged dye, represented by Structure (I'). The leuco form is oxidized, often rapidly oxidized, e.g., by oxygen, to the active fluorescent form.

In some embodiments, the wavelength of electromagnetic radiation used is, e.g., from about 350 nm to about 405 nm, e.g., from around 355 nm to about 375 nm. In other embodiments, photolysis is achieved by the simultaneous absorption of a pair of IR photons, e.g., each having a wavelength of from about 650 to about 800 nm, e.g., from about 700 nm to about 725 nm. Generally, in such a two-photon excitation, the high intensity light required is provided by a laser.

In preferred implementations, a DAPI filter of a wide-field microscope, or a 405 nm laser of a confocal microscope is utilized.

Figure 9:
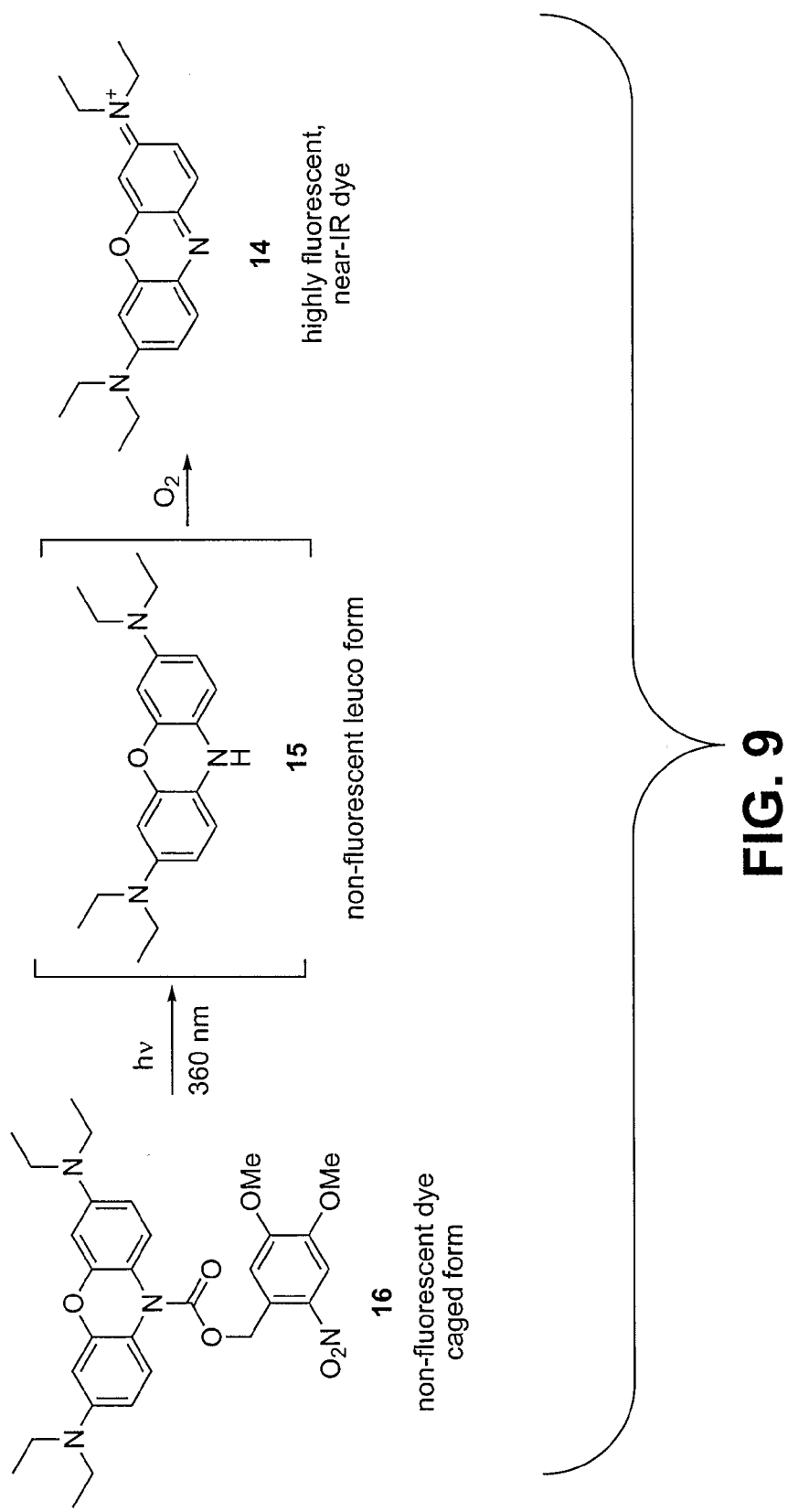
FIG. 9 is a series of structures that illustrate conversion of a specific non-targeting caged dye into its leuco form, followed by oxidation of the leuco form to active form.

FIG. 9 shows a particular example of uncaging a non-fluorescent caged dye to generate the active dye oxazine 1 (14), which fluoresces in the near-IR with a maximal emission at about 665 nm. When novel, non-fluorescent caged dye (16) is irradiated with long-wave UV light (about 360 nm), the NVOC group is photolytically removed, and rapidly decarboxylates to form the oxazine 1 leuco dye (15). The non-fluorescent leuco dye rapidly reacts with oxygen in solution to generate the brightly fluorescent oxazine 1 dye (14). For example, when an acetonitrile solution of the NVOC-caged oxazine 1 derivative (16) was exposed to long-wave UV light, a dramatic and rapid increase in the fluorescence emission in the near-IR (about 665 nm) was observed. In such an evaluation, maximal emission was observed after less than four minutes using a hand-held longwave UV lamp. Irradiation in a fluorescence microscope, with either arc lamp or laser illumination, photoactivates this dye in less than 1 second due to the much higher photon flux through the microscope objective.

Synthesis of Caged, Leuco, and Active Dyes

Figure 10:
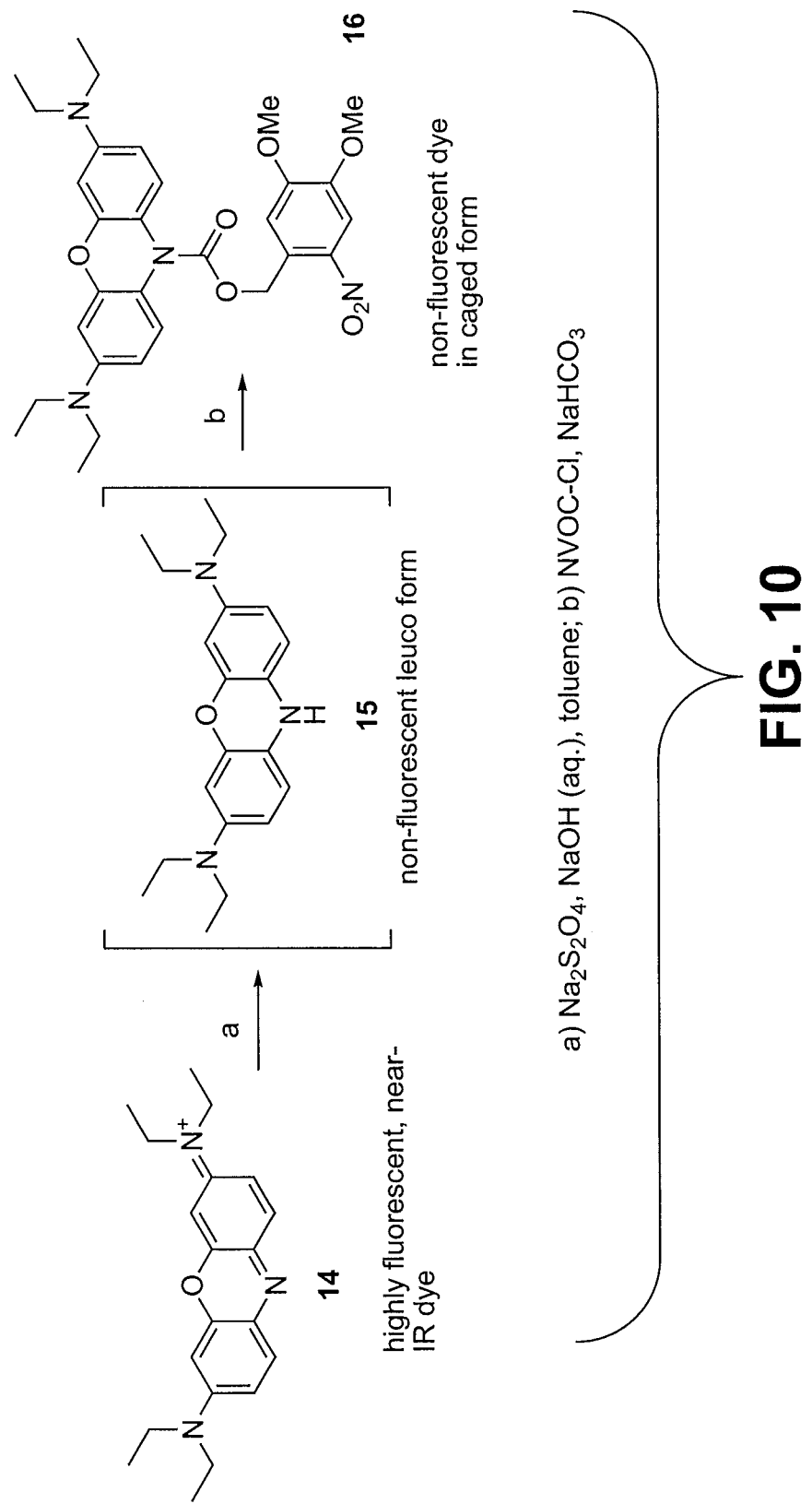
FIG. 10 is a synthetic scheme for producing a specific non-targeting caged dye.

Referring to FIG. 10, non-fluorescent caged leuco dye (16) can be prepared from active oxazine (14) by reducing the active dye with $Na_2S_2O_4$ and base in de-oxygenated toluene. The leuco form (15) is generated in-situ, but it is not isolated. Rather, it is reacted with 6-nitroveratryloxycarbonyl chloride (NVOC-Cl) to generate the desired non-fluorescent caged dye (16).

Figure 11:
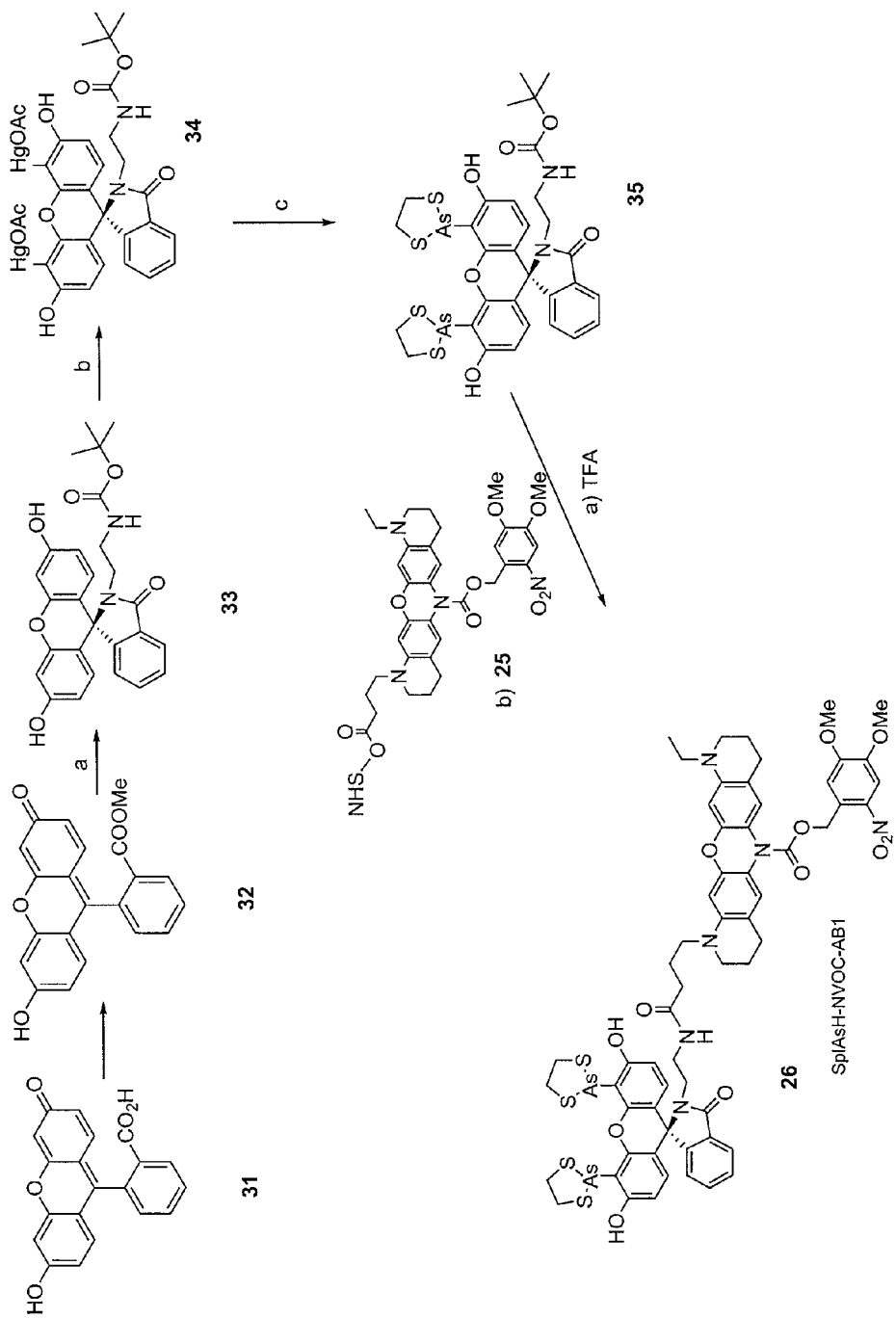
FIG. 11 is a synthetic scheme for producing a specific spirolactam targeting caged dye.

Referring to FIG. 11, non-fluorescent targeting compound (26) can be conveniently and relatively inexpensively synthesized from fluorescein (31). Fluorescein (31) is converted to its methyl ester (32), and then the methyl ester (32) is converted to the 5-membered ring non-fluorophoric spirolactam (33) by treatment with $NH_2(CH_2)_2NHBoc$ (a). Non-fluorophoric spirolactam (33) is converted to the shown corresponding mercury-containing compound (34) by treatment with mercuric acetate in 2% AcOH—$H_2O$ (b). The mercury-containing compound (34) can be converted to the shown arsenic-containing compound (35) by treatment with diisopropylethylamine (DIPEA), arsenic trichloride and $Pd(OAc)_2$, followed by treatment with ethanedithiol (c). Compound (35) is then treated with 30% trifluoroacetic acid (TFA) in dichloromethane to remove the t-butoxycarbonyl group, followed by treatment of the resulting bisarsenical compound 35' with the reactive NHS ester (25) to give the desired dye (26).

Uses of the Caged, Leuco, Active Dyes and Conjugates Thereof

Photoactivatable near-IR dyes bearing amine-reactive NHS esters, thiol-reactive maleimides or iodoacetamides, and the like can allow their ready attachment to proteins and other biomolecules. In addition, photoactivatable near-IR dyes bearing bis-arsenical (or antimony analogs) can allow for the tagging of proteins in-vitro or in living cells, e.g., by targeting tetracysteine peptide tags on the proteins.

Since some of the dyes localize in specific organelles within cells, such as mitochondria, specific organelles can be imaged in real-time. When conjugated to a moiety, such as a protein, that already includes a fluorophore, the dyes can modulate emission from the fluorophore. Thus, if a photoactivatable near-IR fluorophore was targeted to a green, yellow or red fluorescent protein or small molecule fluorophore, its uncaging, e.g. with long-wave UV light, could shift the emission wavelength by fluorescence resonance energy transfer (FRET) from the visible light donor to the photoactivated near-IR acceptor fluorophore. Imaging in the near-IR can be advantageous since autofluorescence is minimal, and tissue penetration is the highest.

Typically, this imaging is performed in live cells using a fluorescence microscope with appropriate filter set.

EXAMPLES

Figure 12:
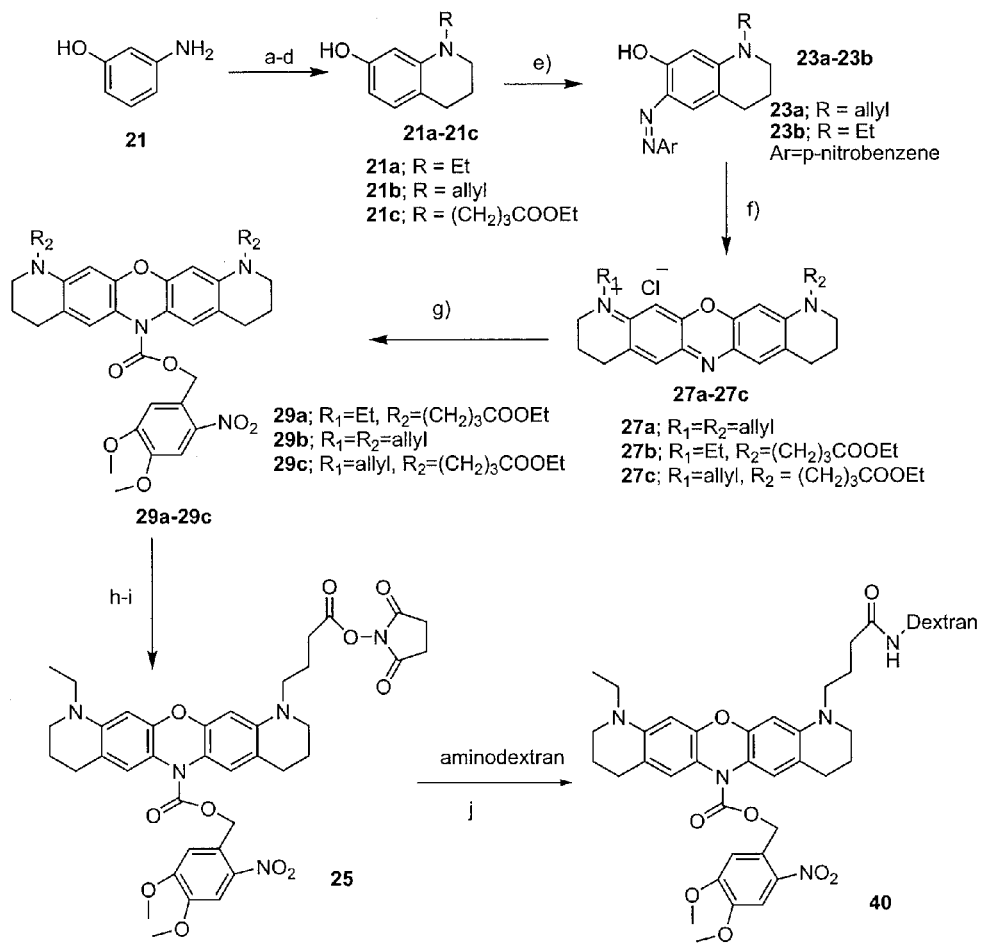
FIG. 12 is a synthetic scheme for producing various dyes and conjugates.

General Procedure for Compounds 21a-21c: (see FIG. 12)

1,2,3,4-Tetrahydro-quinolin-7-ol (6.73 mmol) (obtained in three steps from 21; 21 was obtained from ALDRICH) was suspended in water followed by the addition of sodium bicarbonate (8.08 mmol) and catalytic amount of tetrabutylammonium bromide (TBAB). To the reaction mixture was added the corresponding alkyl bromide (8.08 mmol) dropwise at 0° C. The reaction mixture was brought to room temperature (RT) and left for 12 h. The aqueous reaction mixture was extracted with ethyl acetate, dried with sodium sulfate, and evaporated to dryness. The crude mixture was purified on silica gel (10-35% ethyl acetate-hexanes).

21a (ethyl): Yield=51%.

21b (allyl): Yield=49%. $^1$H NMR (CDCl$_3$): 6.77 (d, 1H, J=7.6 Hz), 6.05-6.02 (m, 2H), 5.8-5.77 (m, 1H), 5.21-5.12 (m, 2H), 3.83-3.81 (m, 2H), 3.25 (t, 2H, J=5.6 Hz), 2.68 (t, 2H, J=5.5 Hz), 1.93 (p, 2H, J=6.2 Hz). $^{13}$C NMR (CDCl$_3$): 155.2, 146.5, 133.4, 129.8, 116.2, 115.2, 102.8, 98.6, 54.1, 49.2, 27.6, 22.7. ES-HRMS [M]$^+$ 190.1214. Calcd for (C$_{12}$H$_{17}$NO): 190.1232.

21c (ethyl butyrate): Yield=57%. 6.76 (d, 1H, J=7 Hz), 6.13 (d, 1H, J=2.3 Hz), 6.03 (dd, 1H, J=7.9 Hz, 2.3 Hz), 4.14 (q, 2H, J=7.1 Hz), 3.25-3.21 (4H, M), 2.66 (t, 2H, J=6.3 Hz, 2.35 (t, 2H, J=7.2 Hz), 1.94-1.81 (m, 4H), 1.26 (t, 2H, J=7.1 Hz). $^{13}$C NMR (CDCl$_3$): 174.1, 155.4, 146.3, 129.9, 114.8, 102.6, 98.0, 60.9, 50.9, 49.6, 31.8, 27.5, 22.6, 21.7, 14.4. ES-HRMS [M]$^+$ 264.1574. Calcd for (C$_{15}$H$_{22}$NO$_3$): 264.1600.

General Procedure for Compounds 23a-23b: (see FIG. 12)

p-Nitrobenzene diazonium salt (1 mmol) was dissolved in 10% sulfuric acid and added to a methanolic solution of 21a/21b (1 mmol). The solution turned red immediately. The reaction mixture was neutralized with ammonia, and the red precipitate was filtered to give quantitative yield of the product.

23a: Yield=Quantitative. $^1$H NMR (DMSO-d$_6$): 8.18 (d, 2H, J=9.1 Hz, 8.10 (s, 1H), 7.61 (d, 2H, J=9.2 Hz), 5.85-5.76 (m, 1H), 5.19-5.10 (m, 2H), 4.01-3.9 (m, 2H), 3.41 (t, 2H, J=5.65 Hz), 3.41 (t, 2H, J=5.6 Hz), 2.67 (t, 2H, J=5.4 Hz), 1.89 (m, 2H, J=6.1 Hz). ES-HRMS [M–H]$^-$ 337.1349. Calcd for (C$_{18}$H$_{17}$N$_4$O$_2$): 372.1301.

23b: Yield=Quantitative. ES-HRMS [M–H]$^-$ 325.1316. Calcd for (C$_{17}$H$_{17}$N$_4$O$_2$): 325.1301.

General Procedure for Oxazine Dyes 27a-27c: (see FIG. 12)

The diazo compound (23a/b, 1 mmol) and the respective quinoline (21a/21c, 1.2 mmol) were taken in an ethanol-water mixture (12 ml+1.2 ml) and heated to 80° C. for 3 h. The reaction mixture turned deep blue. TLC analysis showed no starting material remaining. The solvent was evaporated and the crude mixture was purified on neutral alumina, eluting with 5% methanol-dichloromethane.

27a (bis-allyl): Yield=88%. $^1$H NMR (MeOH-d$_4$): 7.48 (s, 1H), 6.80 (s, 1H), 6.00 (m, 1H), 5.30-5.23 (m, 2H), 4.29-4.28 (m, 2H), 3.67 (t, 2H, J=5.7 Hz), 2.95 (t, 2H, J=5.5 Hz), 2.05 (p, 2H, J=6.3 Hz). $^{13}$C NMR (MeOH-d$_4$): 155.0, 148.7, 134.4, 130.6, 130.1, 129.2, 116.9, 95.5, 54.8, 50.6, 27.19, 20.7. ES-HRMS [M]$^+$ 372.2061. Calcd for (C$_{24}$H$_{26}$N$_3$O$_2$): 372.2076.

27b (ethyl ester): Yield=70%. $^1$H NMR (MeOH-d$_4$): 7.31 (s, 2H), 6.91 (s, 1H), 6.82 (s, 1H), 4.16 (q, 2H, J=7.0 Hz), 3.66-3.59 (m, 6H), 2.87-2.82 (m, 4H), 2.51-2.46 (m, 2H), 2.07-2.01 (m, 8H), 1.31 (t, 3H, J=6.4 Hz), 1.27 (t, 3H, J=7.0 Hz). ES-HRMS [M]$^+$ 434.2422. Calcd for (C$_{26}$H$_{32}$N$_3$O$_3$): 434.2444.

27c: Yield=73%. $^1$H NMR (CDCl$_3$): 7.43 (s, 1H), 7.40 (s, 1H), 6.99 (s, 1H), 6.79 (s, 1H), 6.02-5.91 (m, 1H), 5.33-5.22 (m, 2H), 4.32-4.28 (m, 2H), 4.17 (q, 2H, J=7.1 Hz), 3.71-3.62 (m, 6H), 2.92 (p, 4H, J=5.9 Hz), 2.51 (t, 2H, J=6.6 Hz), 2.09-1.97 (m, 6H), 1.26 (t, 3H, J=7.1 Hz). ES-HRMS [M]$^+$ 446.2420. Calcd for (C$_{27}$H$_{32}$N$_3$O$_3$): 446.2444.

General Procedure for Photocaged Oxazine Dyes 29a-29c: (see FIG. 12)

Oxazine dyes (27a-27c, 0.2 mmol) were dissolved in water (3 ml) and methanol (1 ml). To the blue solution, toluene (20 ml) and solid sodium dithionate (2.85 mmol) were added. The reaction mixture was sparged with argon for 10-15 minutes followed by heating to 50° C. until the solution became yellow (2-3 h). The reaction mixture should be completely devoid of oxygen, or re-oxidation to the blue oxazine dye will occur. The solution was cooled to RT, and solid sodium bicarbonate was added followed by the addition of a toluene solution of NVOC-Cl (0.24 mmol). The reaction mixture was again sparged with argon and stirred at RT for another 3 h. The organic layer was separated, and the aqueous layer was washed three times with ethyl acetate. The combined organic layers were dried with sodium sulfate, evaporated and then purified by silica gel chromatography (15-40% ethyl acetate/hexanes).

29a: Yield=18%. $^1$H NMR (CDCl$_3$): 7.7 (s, 1H), 7.10 (s, 2H), 6.86 (s, 1H), 6.20 (s, 2H), 5.84-5.75 (m, 2H), 5.69 (s, 2H), 5.18-5.12 (m, 4H), 3.93 (s, 3H), 3.81-3.80 (m, 4H), 3.71 (s, 3H), 3.23 (t, 4H, J=5.3 Hz), 2.70 (t, 4H, J=5.1 Hz), 1.92 (p, 4H, J=6.02 Hz).

29b: Yield=46%. $^1$H NMR (CDCl$_3$): 7.70 (s, 1H), 7.09 (s, 1H), 7.08 (s, 1H), 6.87 (s, 1H), 6.25 (s, 1H), 6.24 (s, 1H), 5.68 (s, 2H), 4.14 (q, 2H, J=7.1 Hz), 3.92 (s, 3H), 3.73 (s, 3H), 3.31-3.19 (m, 8H, 2.68 (t, 4H, J=6.0 Hz), 2.34 (t, 2H, J=6.2 Hz), 1.93-1.86 (m, 6H), 1.26 (t, 3H, J=7.1 Hz), 1.10 (t, 3H, J=7.0 Hz). ES-HRMS [M+H]$^+$ 613.2668. Calcd for (C$_{34}$H$_{37}$N$_4$O$_7$): 613.2662.

29c: Yield=23%. $^1$H NMR (CDCl$_3$): 7.70 (s, 1H), 7.09 (s, 1H), 7.08 (s, 1H), 6.87 (s, 1H), 6.23 (s, 1H), 6.21 (s, 1H), 5.85-5.75 (m, 1H), 5.69 (s, 2H), 5.20-5.12 (m, 2H), 4.12 (q, 2H, J=7.05 Hz), 3.93 (s, 3H), 3.82-3.78 (m, 3H), 3.73 (s, 3H), 3.25-3.18 (m, 6H), 2.72-2.63 (m, 4H), 2.34 (t, 2H, J=6.3 Hz), 1.95-1.84 (m, 6H), 1.27 (t, 3H, J=7.2 Hz).

Synthesis of Amine-Reactive Photocaged Oxazine NHS Ester 25: (see FIG. 12)

Compound 29a (0.0118 mmol) was refluxed in acetone (0.5 mL) and water (0.25 mL) in the presence of 2.5 M HCl (0.015 mL) for 3 h. During this period the ethyl ester was hydrolyzed to the respective acid. The solvents were removed under vacuum and the dried free acid was used to make the corresponding NHS ester without further purification. The free acid was dissolved in a mixture of dichloromethane (2 mL) and DMF (1 mL) followed by the addition of N-hydroxysuccinimide (0.038 mmol) and DIC (0.028 mmol). The reaction mixture was heated at 50° C. overnight. The solvent was evaporated and purified by flash chromatography using 45% acetone/hexanes.

25 (NHS ester): Yield=71% (two steps). $^1$H NMR (CDCl$_3$): 7.70 (s, 1H), 7.10 (s, 1H), 7.08 (s, 1H), 6.87 (s, 1H), 6.26 (s, 1H), 6.22 (s, 1H), 5.68 (s, 2H), 3.92 (s, 3H), 3.73 (s, 3H), 3.33-3.17 (m, 8H), 2.84 (s, 4H), 2.71-2.65 (m, 4H), 2.02 (p, 2H, J=7.0 Hz), 1.95-1.87 (m, 4H), 1.12 (t, 3H, J=7.1 Hz). ES-HRMS [M−H]$^-$ 742.2724. Calcd for ($C_{38}H_{40}N_5O_{11}$): 742.2725.

Conjugation of 25 to Aminodextran 40: (see FIG. 12)

Aminodextran (0.25 µmol) from a 25 mg/mL aqueous solution was added to 1 µmol of caged-oxazine NHS ester 25 (12 mg/mL stock in DMSO) followed by the addition of 104, of 0.1 M sodium bicarbonate. The reaction mixture was stirred at RT for 1.5 h. The crude mixture was gel-filtered through three Zeba™ micro desalt spin columns (Pierce). Two volumes of ethanol (2004) were then added to the gel-filtered aqueous solution of conjugated aminodextran. The solution became turbid which was centrifuged to yield a white precipitate of conjugated aminodextran. The white solid was washed three times with methanol and dried under low vacuum. The white solid was dissolved in water to give a homogeneous solution of conjugated dextran with the final concentration of 12 mg/mL.

Figure 13:
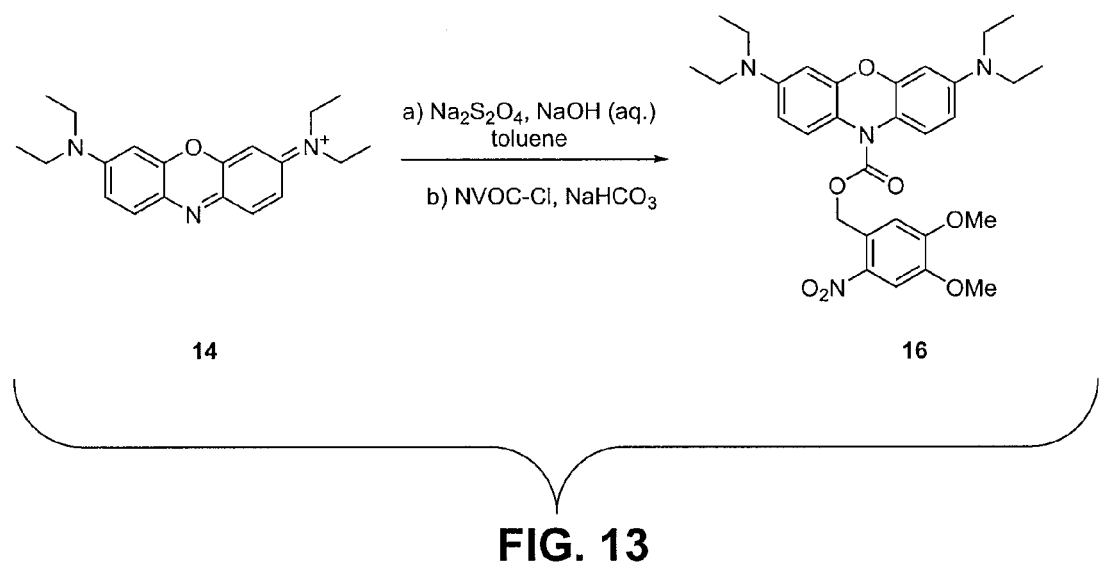
FIG. 13 is a synthetic scheme for producing a specific caged dye.

Synthesis of NVOC-Oxazine 16: (see FIG. 13)

The oxazine perchlorate (50 mg, 0.12 mmol) was dissolved in water (1.5 mL). To the blue solution, toluene (10 ml), 40% sodium hydroxide (1.5 ml) and mixture was sparged with argon for 10-15 minutes followed by heating to 50° C. until the sodium dithionate (60 mg, 0.34 mmol) was added. The reaction n became yellow (2-3 h). Solid sodium bicarbonate (35 mg, 0.41 mmol) was then added followed by the addition of a toluene solution of NVOC-Cl (40 mg, 0.14 mmol) at RT. The reaction mixture was again sparged with argon and stirred at RT for another 3 h. The organic layer was separated and the aqueous layer was washed three times with ethyl acetate. The combined organic layers were dried by sodium sulfate, evaporated and then purified by silica gel chromatography using 20% EtOAc/hexanes. Yield=41 mg (61%). $^1$H NMR (CDCl$_3$): 7.70 (s, 1H), 7.36 (d, 2H, J=8.8 Hz), 6.89 (s, 1H), 6.38-6.34 (m, 4H), 5.71 (s, 2H), 3.92 (s, 3H), 3.70 (s, 3H) 3.30 (q, 8H, J=7.05 Hz), 1.14 (t, 12H, J=7.01 Hz).

Synthesis of SplAsH-Photocaged Oxazine 26:

The NHS ester 25 (3 mg, 0.004 mmol) was treated with the SplAsH amine (8.5 mg, 0.012 mmol) and DIPEA (2 µL, 0.012 mmol) in dichloromethane (1 mL) for 4 h at RT followed by purification by preparative TLC using 40% EtOAc-hexanes to yield 4.1 mg of the desired SplAsH-tethered photocaged oxazine dye. ES-HRMS [M+Na]$^+$ 1357.1547. Calcd for ($C_{60}H_{60}As_2N_6NaO_{12}S_4$): 1357.1482.

Figure 14:
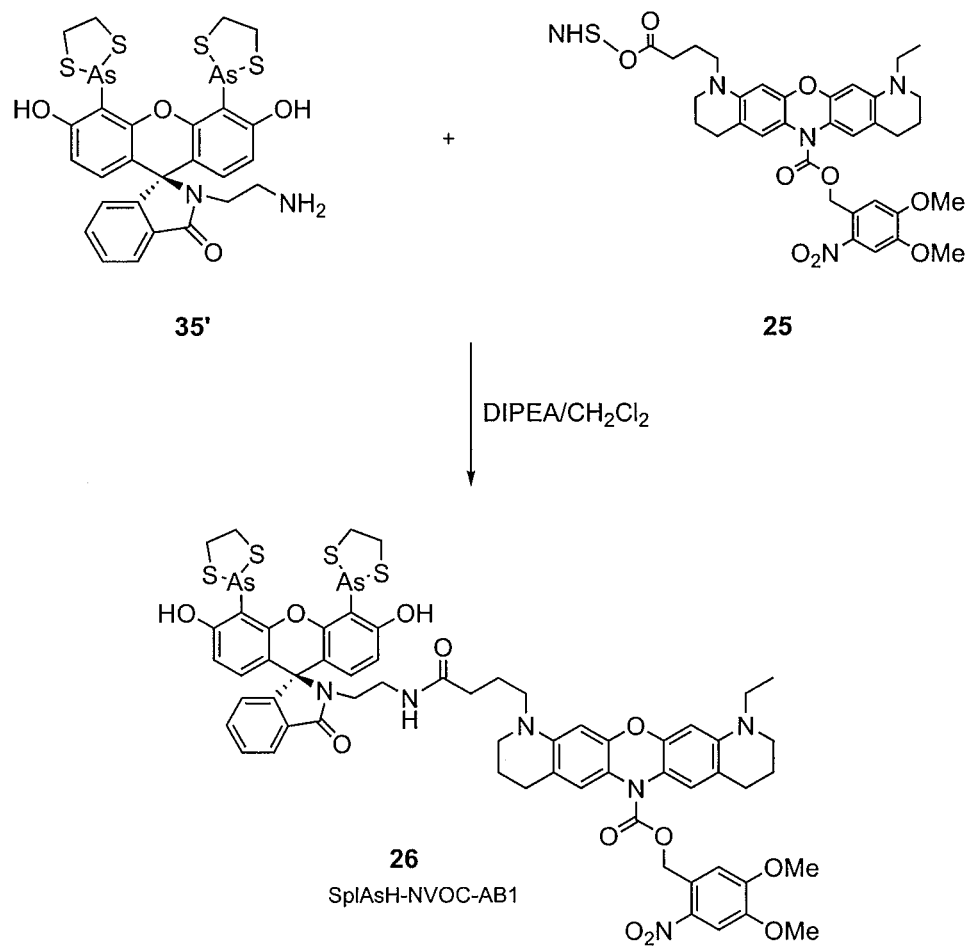
FIG. 14 is a synthetic scheme for producing a specific caged targeting dye.

Synthesis of Thiol-Reactive Photocaged Oxazine Maleimide: (see FIG. 14)

The NHS ester 25 (3 mg, 0.004 mmol) was treated with the N-(2-aminoethyl)maleimide trifluoroacetate salt (3.1 mg, 0.012 mmol) and DIPEA (2 µL, 0.012 mmol) in dichloromethane (0.25 mL) and acetonitrile (1 mL) for 1 h at RT followed by purification by preparative TLC using 100% EtOAc to yield 2 mg of the maleimide-conjugated dye.

Photoactivation of NVOC-Oxazine 16 in vitro: (see FIGS. 15A-15B)

Figure 15A:
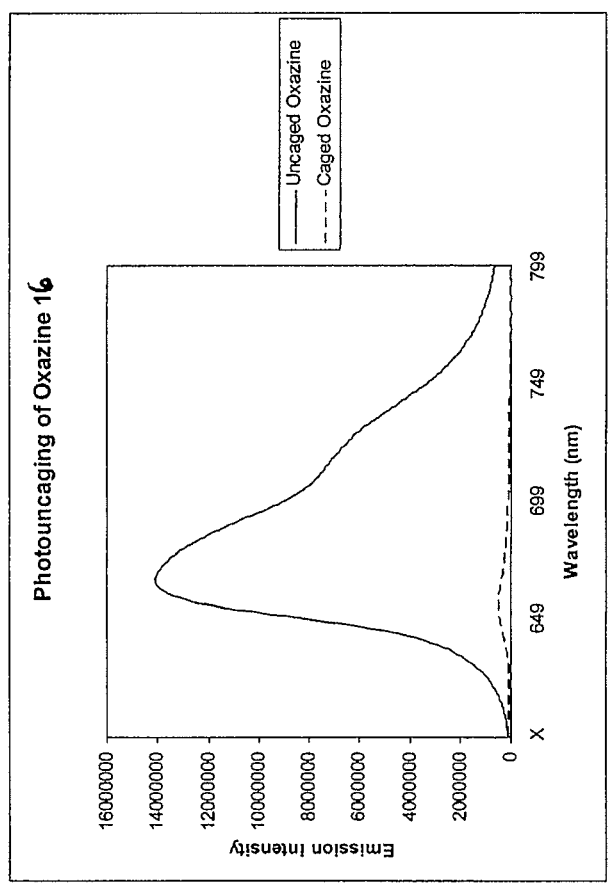
FIG. 15A is a fluorescence emission spectrum of the caged and uncaged oxazine dye 16.
Figure 15B:
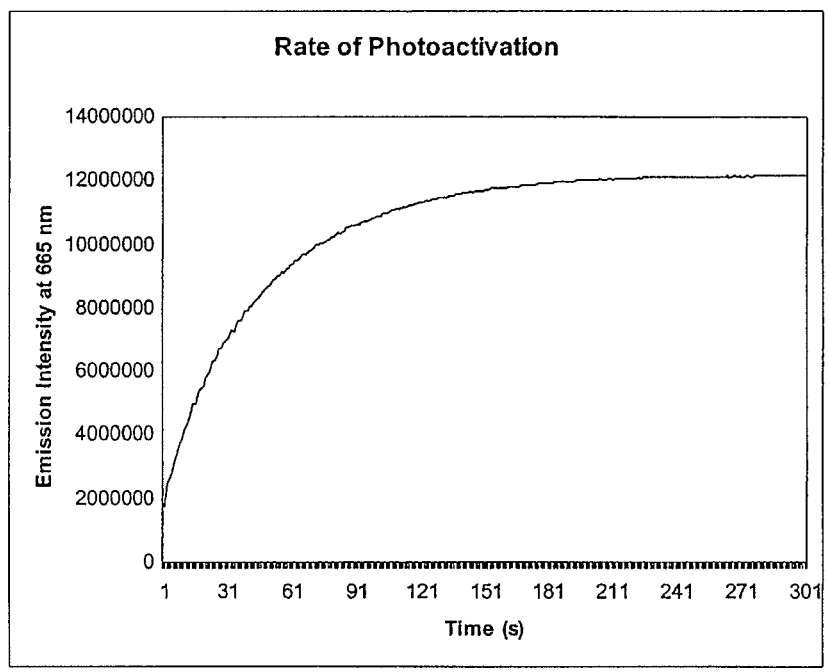
FIG. 15B is a plot of emission intensity versus time of the oxazine dye 16, illustrating rate of photoactivation.

Referring to FIGS. 15A and 15B, NVOC-Oxazine 16 was dissolved in acetonitrile (2 mL) and placed in a fluorescence cuvette. The rate of photo-uncaging was monitored by continuous excitation at 365 nm and emission detection at 665 nm in a SPEX Fluoromax-3. Under these conditions, fluorescence activation reached a maximum in approximately two minutes.

Photoactivation in Live Mammalian Tissue Culture Cells: (see FIGS. 16A-16B, and FIG. 21)

Figure 16A:
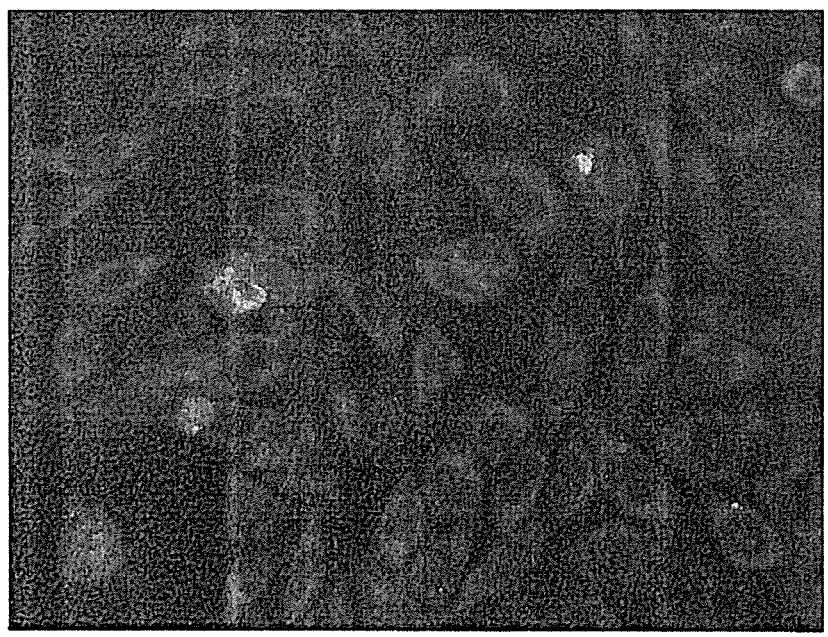
FIGS. 16A and 16B are NIR fluorescence micrographs of CHO-K1 cells before (FIG. 16A) and after (FIG. 16B) photoactivation.
Figure 16B:
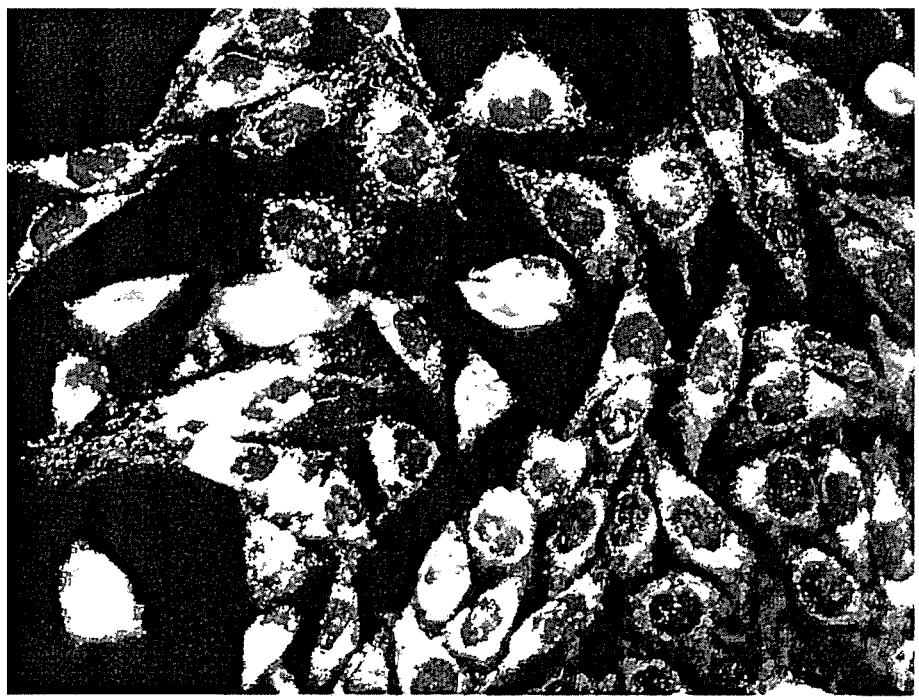
Figures 17A, 17B, 17C, 17D, 17E, 17F:
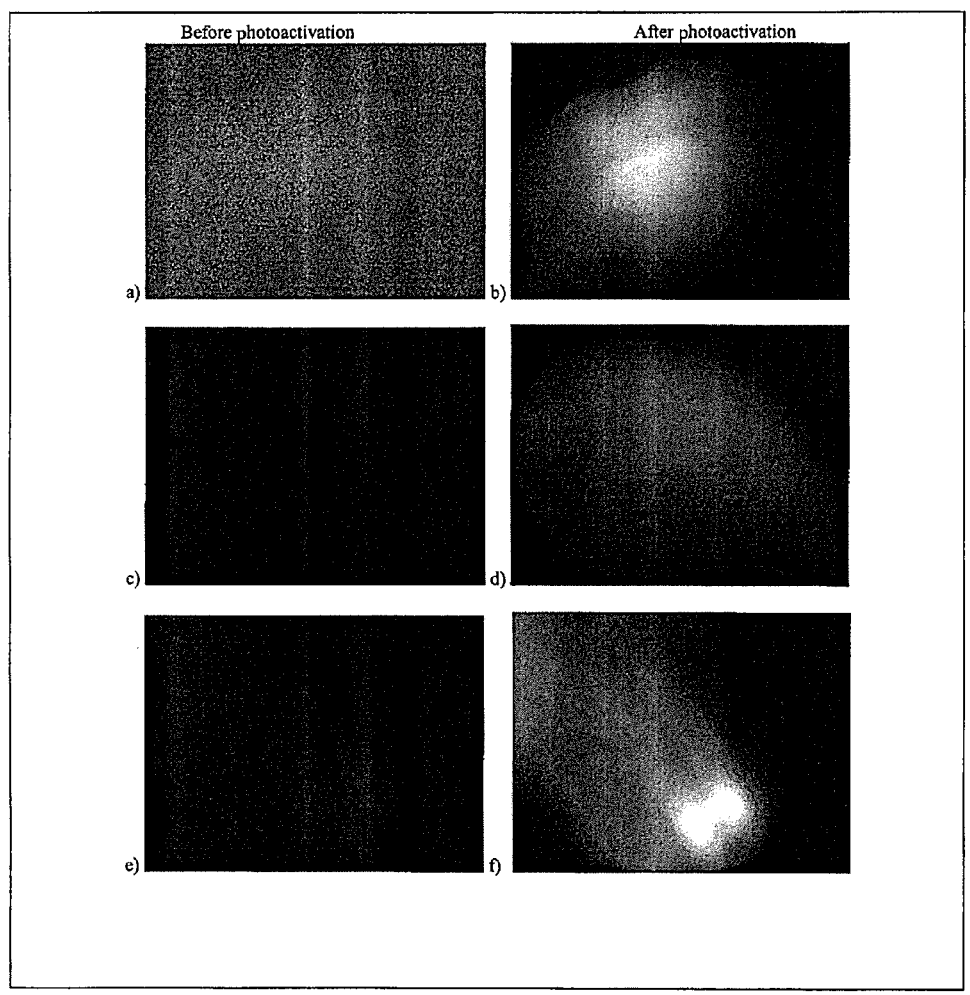
FIGS. 17A-17F are micrographs of zebrafish embryos before (FIGS. 17A, C and E) and after photoactivation (FIGS. 17B, D and F), taken 2, 4 and 24 hours post-fertilization.

Referring to FIGS. 16A (before) and 16B (after photoactivation), CHO-K1 cells were incubated with 1 µM of NVOC-Oxazine 16 for one hour, then imaged on a fluorescence microscope at 40× with a Cy5 filter set (Zeiss Axiovert 200M). Brief exposure to DAPI-filtered light (365 nm, <1 second) caused a dramatic increase in cellular fluorescence. The caged oxazines 29a, 29b and 53 were cell-permeable similar to 16, and photoactivation resulted in apparent mitochondrial staining In contrast, the caged oxazine 25 gave more diffuse staining (FIG. 20), as did 41. All of these latent fluorophores are chemically stable in cells, and can be efficiently photoactivated 24 hours after initial incubation.

Photoactivation in Developing Zebrafish Embryos: (see FIGS. 17A-17F)

Referring to FIGS. 17A-17F, aminodextran-conjugated caged oxazine dye 40 was microinjected into zebrafish embryos at the one-cell stage. At various stages in development, the embryo was mounted on a fluorescence microscope and imaged (10×, Cy5 filter) before and after exposure to DAPI-filtered light.

Figure 20:
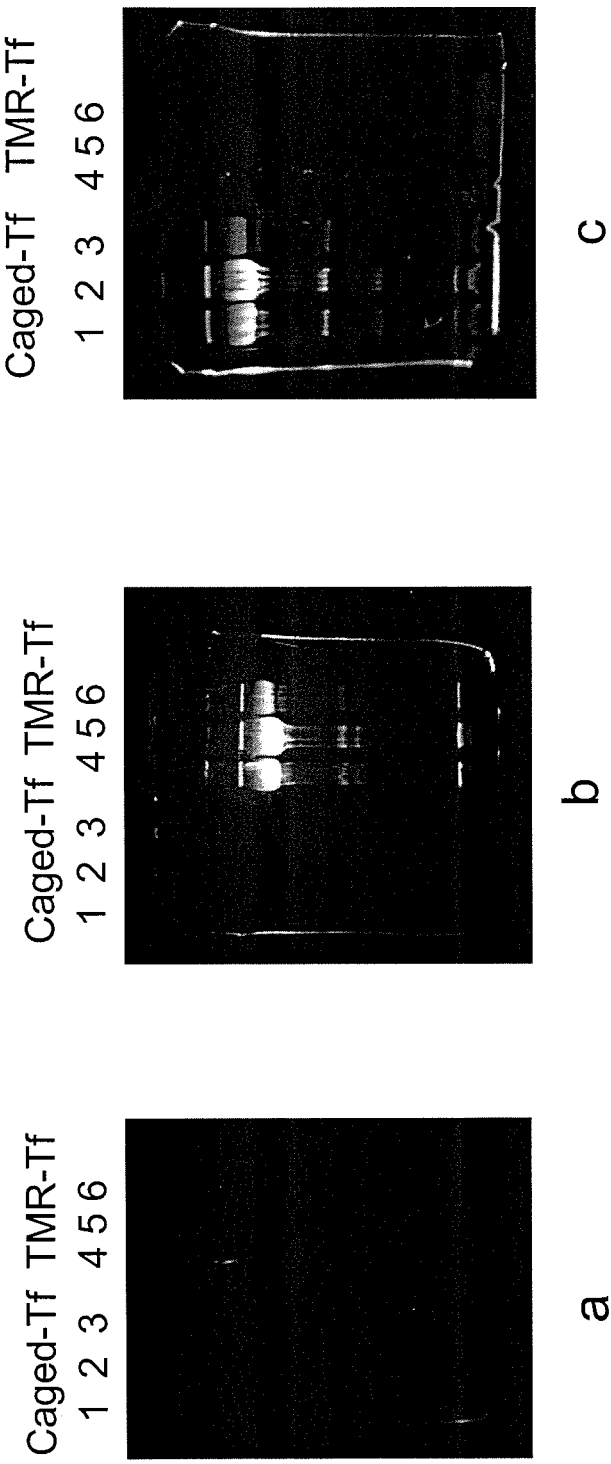
FIG. 20 is an SDS-PAGE gel of transferrin labeled with a caged oxazine dye, imaged before and after photoactivation. Transferrin in lanes 1-3 is labeled with NVOC-MR121 (25). Lanes 4-6 are labeled with tetramethyl-rhodamine (TMR). No near-IR fluorescence is visible from the caged dye prior to photoactivation (a: 630 nm excitation, 670 nm long pass filter), whereas TMR-Tf is readily visible (b: 520 nm excitation and a 575DF20 filter). After exposure to a hand-held long-wave UV lamp for 1 minute, the labeled transferrin becomes brightly fluorescent in the near-IR (c: 630 nm excitation, 670 nm long pass filter).

Labeling of Transferrin with NVOC-MR121 NHS Ester 25:

Transferrin (Sigma-Aldrich®, 5 mg) was dissolved in 0.5 ml of 0.1M NaHCO$_3$, pH 8.3. The caged oxazine dye 25 (0.2 mg) in 0.02 ml of DMSO and added to the transferrin solution and incubated at room temperature for one hour. The labeled protein was separated from the dye on a PD-10 column, and analyzed by SDS-PAGE (FIG. 20). The transferrin conjugate was initially non-fluorescent (FIG. 20a). Photoactivation with a hand-held longwave UV lamp for 1 min resulted in bright near-IR fluorescence (FIG. 20c).

Figure 18:
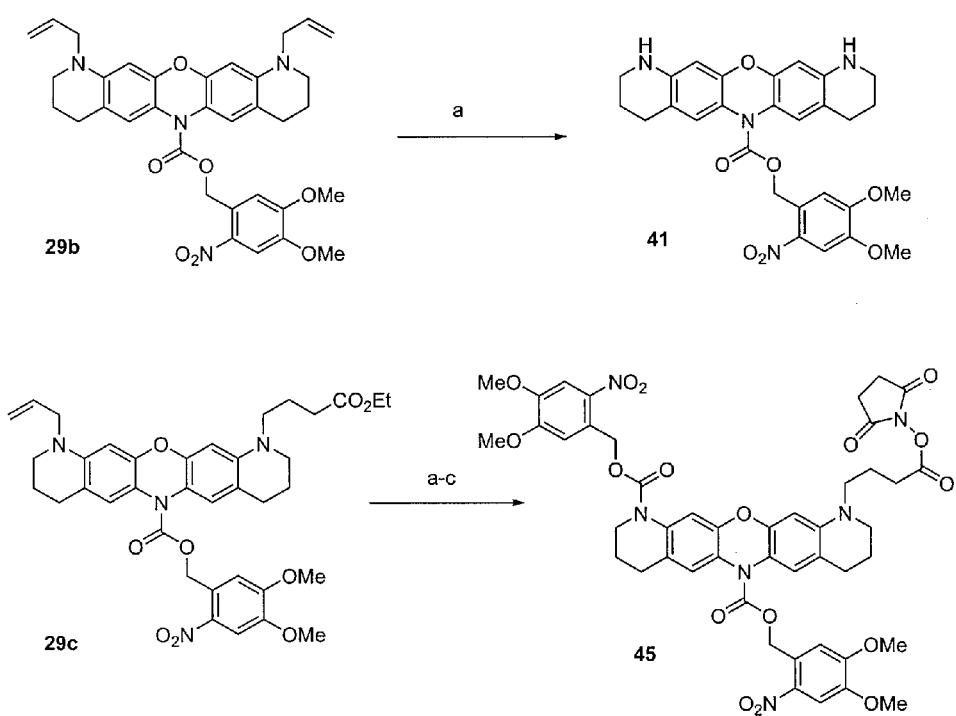
FIG. 18 is a synthetic scheme for producing various dyes and conjugates.
Figure 19:
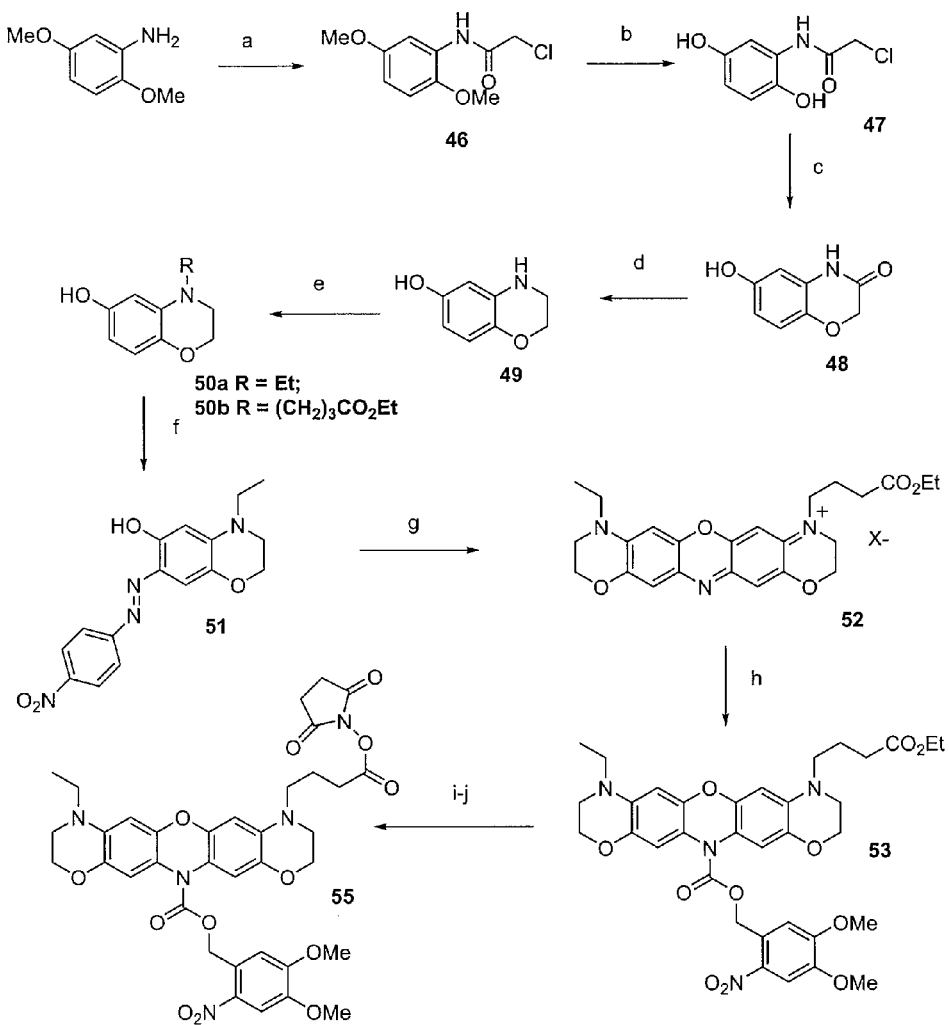
FIG. 19 is a synthetic scheme for producing various dyes and conjugates.

Synthesis of Bis-NH NVOC-Oxazine 41: (see FIG. 18). Compound 29b (30 mg, 0.04 mmol) was taken in water (5 ml) followed by the addition of 10 mg bis(allyl) Ru(IV) catalyst (Cadierno et al., *Chem. Commun.* 2005, p 4086). The reaction mixture was heated to 100° C. for 3 h. The solvent was evaporated and the crude was purified by prep TLC to yield 8 mg of the pure 41. ES-HRMS [M+H]$^+$ 533.2050. Calcd for ($C_{28}H_{29}N_4O_7$): 533.2036.

Deallylation of 29c: Compound 29c (0.068 g, 0.09 mmol) and bis(allyl) Ru(IV) catalyst (0.005 g.) were added to water (5 ml). The mixture was heated at 100° C. for 1.5 h. The water was evaporated and the crude was dissolved in dichloromethane and purified on a silica gel column using 50% (v/v) EtOAc-hexanes to yield pure compound 42. Yield: 0.033 g, 56%. $^1$H NMR (CDCl$_3$): 7.70 (s, 1H), 7.09 (s, 1H), 7.08 (s, 1H), 6.87 (s, 1H), 6.23 (s, 1H), 6.14 (s, 1H), 5.68 (s, 2H), 4.14 (q, 2H, J=7.0 Hz), 3.93 (s, 3H), 3.74 (s, 3H), 3.28-3.18 (m, 6H), 2.73-2.63 (m, 4H), 2.34 (t, 2H, J=6.3 Hz), 1.92-1.84 (m, 6H), 1.26 (t, 3H, 7.1 Hz). ES-HRMS [M+H]$^+$ 647.2677. Calcd for ($C_{34}H_{39}N_4O_9$): 647.2717.

Synthesis of Bis-NVOC Oxazine ethyl ester 43: Compound 42 (0.028 g, 0.04 mmol) was dissolved in acetonitrile-water (5+3) ml mixture followed by the addition of solid sodium bicarbonate (0.007 g, 0.08 mmol) and NVOC-Cl (0.048 g, 0.17 mmol). The reaction mixture was stirred at RT for 2 h. The solvent was evaporated and extracted in dichloromethane. The crude was purified in silica gel column using 50% EtOAc-Hexanes. Yield=0.031 g, 87%. $^1$H NMR (CDCl$_3$): 7.28 (s, 1H), 7.72 (s, 1H), 7.70 (s, 1H), 7.45 (s, 1H), 7.05 (s, 1H), 6.98 (s, 1H), 6.86 (s, 1H), 6.24 (s, 1H), 5.67 (s, 2H), 5.64 (s, 2H), 4.13 (q, 2H, J=7.1 Hz), 3.92 (s, 3H), 3.94 (s, 3H), 3.81-3.76 (m, 5H), 3.76 (s, 3H), 3.25-3.20 (m, 4H), 2.75 (t, 2H, J=6.2 Hz), 2.67 (t, 2H, J-6.1 Hz), 2.30 (t, 2H, J=6.2 Hz), 1.97-1.84 (m, 6H), 1.25 (t, 3H, J=6.3 Hz). ES-HRMS [M+H]$^+$ 886.3169. Calcd for (C$_{44}$H$_{48}$N$_5$O$_{15}$): 886.3147.

Synthesis of Bis-NVOC-Oxazine NHS ester 45: (see FIG. 18). Compound 43 (0.015 g, 0.017 mmol) was refluxed in acetone-water (0.5 mL+0.25 mL) in the presence of 2.5 M HCl (0.015 mL) for 3 h. During this period the ethyl ester was hydrolyzed to the respective acid 44. The free acid was used to make the corresponding NHS ester without further purification. The free acid was dissolved in dichloromethane (2 ml) followed by the addition of N-hydroxysuccinimide (0.038 mmol) and DIC (0.028 mmol). The reaction mixture was heated at 45° C. for 3 h. The solvent was evaporated and purified by flash chromatography using 45/55 (v/v) acetone-hexane. Yield=6.3 mg. (40%). $^1$H NMR (CDCl$_3$): 7.28 (s, 1H), 7.73 (s, 1H), 7.70 (s, 1H), 7.45 (s, 1H), 7.05 (s, 1H), 6.98 (s, 1H), 6.86 (s, 1H), 6.24 (s, 1H), 5.67 (s, 2H), 5.64 (s, 2H), 3.92 (s, 3H), 3.94 (s, 3H), 3.81-3.76 (m, 5H), 3.76 (s, 3H), 3.28-3.22 (m, 4H), 2.82 (s, 4H), 2.78 (t, 2H, J=6.2 Hz), 2.67 (t, 2H, J-6.1 Hz), 2.32 (t, 2H, J=6.2 Hz), 1.97-1.83 (m, 6H). ES-HRMS [M+H]$^+$ 955.3019. Calcd for (C$_{46}$H$_{47}$N$_6$O$_{17}$): 955.2997. ES-HRMS of the free acid [M+H]$^+$ 858.2813. Calcd for (C$_{42}$H$_{43}$N$_5$O$_{15}$): 858.2834.

Synthesis of 2-Chloro-N-(2,5-dimethoxy-phenyl)-acetamide (46). 2,5-dimethoxyaniline (20 g., 130.56 mmol) was suspended in water (300 ml) followed by the addition of sodium bicarbonate (13.4 g., 156.6 mmol)) and tetrabutylammonium bromide (catalytic amount). To the mixture was added chloroacetyl chloride (12.4 ml, 156.6 mmol) dropwise at 0° C. The reaction mixture was stirred at room temperature for 1 h. The solid suspension was filtered off to yield pure 46. Yield=23.6 g (79%). $^1$H NMR: 9.46 (1H), 7.68 (1H, d, J=2.96 Hz), 6.96 (1H, d, J=8.96 Hz), 6.43 (1H, dd, J=8.95 and 3.06 Hz), 4.37 (s, 2H), 3.79 (s, 3H), 3.67 (s, 3H). $^{13}$C NMR: 43.3, 55.9, 56.2, 106.0, 111.0, 127.4, 127.7, 142.7, 154.0, 163.8. ES-HRMS [M+H]$^+$ 230.0509. Calcd for (C$_{10}$H$_{13}$NO$_3$): 230.0578.

Synthesis of 2-Chloro-N-(2,5-dihydroxy-phenyl)-acetamide (47). Compound 46 (5 g, 21.7 mmol) was dissolved in dichloromethane followed by the dropwise addition of boron tribromide (1M solution in dichloromethane, 84 ml, 84 mmol) at 0° C. The reaction mixture was left at 4° C. overnight. Water (100 ml) was added carefully to destroy excess boron tribromide. The solid precipitation was filtered off to yield brownish pure compound. Yield=4.15 g. (94%). $^1$H NMR (dmso-d$_6$): 9.29 (s, 1H), 9.20 (s, 1H), 8.77 (s, 1H), 7.46 (d, 1H, J=3.02 Hz), 6.65 (d, 1H, J=8.89 Hz), 6.33 (dd, 1H, J=8.95 and 2.98 Hz), 4.35 (s, 2H). $^{13}$C NMR (dmso-d6): 165.0, 150.3, 150.2, 140.2, 126.6, 116.2, 111.6, 44.1. ES-HRMS [M+H]$^+$202.0271. Calcd for (C$_8$H$_9$NO$_3$):202.0278.

Synthesis of 6-Hydroxy-4H-benzo[1,4]oxazin-3-one (48). Sodium hydride (60%) (1.6 g, 39.68 mmol) was added to a THF solution of compound 47 (2.5 g, 12.4 mmol) at 0° C. The reaction mixture was warmed to room temperature and left for 12 h. Excess sodium hydride was destroyed by careful addition of ice-water. The crude reaction mixture was acidified by the addition 1M HCl. The reaction mixture was extracted in EtOAc (6×50 ml). Solvent was evaporated to yield a brownish solid which was used for the next step without further purification. Yield=1.61 g. (78%). $^1$H NMR (dmso-d$_6$): 10.5 (s, 1H), 9.14 (s, 1H), 6.71 (d, 1H, J=8.86 Hz), 6.34 (d, 1H, J=2.73 Hz), 6.26 (dd, 1H, J=8.83 and 2.62 Hz), 4.41 (s, 1H). $^{13}$C NMR (dmso-d6): 166.1, 153.2, 136.5, 128.5, 117.2, 109.8, 103.5, 67.5. ES-HRMS [M+H]$^+$ 166.0500. Calcd for (C$_8$H$_8$NO$_3$): 166.0478.

Synthesis of 3,4-Dihydro-2H-benzo[1,4]oxazin-6-ol (49). Compound 48 (0.39 g, 2.35 mmol) was dissolved in THF and 1M BH$_3$-THF (7.05 ml, 7.05 mmol) was added to the reaction mixture at 0° C. slowly over a time of 5 min. After the addition the reaction mixture was warmed to the room temperature and left overnight. Excess borane was destroyed by careful addition of methanol. The solvent was removed and the crude reaction mixture was extracted in EtOAc to give an oily pure compound in quantitative yield (0.34 g.). $^1$H NMR (dmso-d$_6$): 8.48 (s, 1H), 6.37 (d, 1H, J=8.47 Hz), 5.96 (d, 1H, J=2.75 Hz), 5.82 (dd, 1H, J=8.44, 2.76 Hz), 3.97 (t, 2H, J=4.38 Hz), 3.18 (t, 2H, J=4.31 Hz). $^{13}$C NMR (dmso-d6): 152.2, 136.6, 135.8, 116.7, 103.8, 102.0, 65.0, 47.2. ES-HRMS [M+H]$^+$ 152.0711. Calcd for (C$_8$H$_{10}$NO$_2$): 152.0711.

General procedure for synthesis of 50a and 50b: Compound 49 (3.04 mmol) was dissolved in DMF followed by the addition of 3.65 mmol ethyl bromide (for 50a) or ethyl bromopropionate (for 50b) and potassium carbonate (3.04 mmol). The reaction mixture was heated at 55° C. for 18 h. The crude reaction mixture was poured onto water (25 ml). The aqueous layer was neutralized by the addition of 1M HCl. The aqueous layer was extracted in ethyl acetate four times (4×25 ml). The combined organic layer was dried by the addition of sodium sulfate and evaporated. The crude oily compound was purified by 15%-25% EtOAc-hexanes.

Synthesis of 4-Ethyl-3,4-dihydro-2H-benzo[1,4]oxazin-6-ol (50a): Yield=38%. $^1$H NMR (dmso-d$_6$): 8.57 (s, 1H), 6.40 (d, 1H, J=8.75 Hz), 6.08 (d, 1H, J=3.01 Hz), 5.87 (dd, 1H, J=2.83 and 8.92 Hz), 4.03 (t, 2H, J=4.48 Hz), 3.24-3.18 (m, 4H), 1.02 (t, 3H, J=7.05 Hz). $^{13}$C NMR (dmso-d6): 152.5, 137.3, 135.8, 116.6, 116.4, 105.0, 64.4, 46.1, 44.6, 10.7. ES-HRMS [M+H]$^+$ 180.1024. Calcd for (C$_{10}$H$_{14}$NO$_2$): 180.1024.

Synthesis of 4-(6-Hydroxy-2,3-dihydro-benzo[1,4]oxazin-4-yl)-butyric acid ethyl ester (50b): Yield=28%. $^1$H NMR (dmso-d$_6$): 8.57 (s, 1H), 6.40 (d, 1H J=8.4 Hz), 6.10 (d, 1H, J=2.60 Hz), 5.87 (dd, 1H, J=5.7 and 2.6 Hz), 4.06-3.98 (m, 4H), 3.21 (t, 2H, J=4.6 Hz), 3.15 (t, 2H, J=7.1 Hz), 2.23 (t, 2H, J=7.2 Hz), 1.74 (p, 2H, J=7.2 Hz), 1.15 (t, 2H, 6.1 Hz). $^{13}$C NMR (dmso-d6): 173.3, 152.6, 137.1, 136.1, 116.6, 116.3, 99.97, 64.3, 60.5, 60.43, 47.2, 31.6, 21.6, 14.7. ES-HRMS [M+H]$^+$ 266.1385. Calcd for (C$_{14}$H$_{19}$NO$_4$): 266.1392.

Synthesis of 4-Ethyl-7-(4-nitro-phenylazo)-3,4-dihydro-2H-benzo[1,4]oxazin-6-ol (51): p-Nitrobenzenediazonium tetrafluoroborate (0.251 g, 1.06 mmol) was dissolved in 10% sulfuric acid (10 ml) and added to a methanolic solution (10 ml) of 50a (0.19 g, 1.06 mmol). The solution turned red immediately. The reaction mixture was neutralized with ammonia. The red precipitate was filtered to give quantitative yield of the product. ES-HRMS [M−H]$^−$ 327.1428. Calcd for (C$_{16}$H$_{15}$N$_4$O$_4$): 327.1094.

Synthesis of Oxazine dye 52: The diazo compound 51 (0.157 g, 0.48 mmol) and compound 50b (0.131 g, 0.48 mmol) were taken in ethanol-water mixture (1 ml+0.1 ml). Concentrated HCl (0.22 ml) was added and the solution heated to 75° C. for 1.5 h. The reaction mixture turned deep blue. TLC analysis showed no starting material left. Solvent was evaporated and the crude mixture was purified on silica gel using 15% dichloromethane-methanol (v/v). Yield=0.137 g. (60%). $^1$H NMR (CD$_3$OD): 7.20 (s, 1H), 7.12 (s, 3H), 4.36 (q, 4H, J=4.1 Hz), 4.17 (q, 2H, J=7.1 Hz), 3.86-3.72 (m, 8H), 2.52 (t, 2H, 6.4 Hz), 2.06 (q, 2H, J=6.7 Hz), 1.38 (t, 3H, J=7.1 Hz), 1.26 (t, 2H, J=7.1 Hz), 13C NMR: 173.4, 146.8, 146.7, 146.6, 146.4, 146.2, 146.1, 145.8, 113.6, 113.4, 94.9, 63.6, 60.6, 51.5, 30.1, 21.1, 13.3, 10.5. ES-HRMS [M]$^+$ 438.2032. Calcd for (C$_{24}$H$_{28}$N3O$_5$): 438.2029. 650 nm (ex), 665 nm (em). Extinction Coefficient: 108,000 (Ethanol), 89,000 (20 mM PBS). Quantum Yield=0.52 (Ethanol) and 0.58 (PBS), referenced to oxazine 1.

Synthesis of NVOC caged oxazine dye 53: Oxazine dye 52 (0.052 g, 0.11 mmol) was dissolved in water (3 ml). To the blue solution, toluene (20 ml) and solid sodium dithionate (0.058 g, 0.33 mmol) were added. The reaction mixture was sparged with argon for 10-15 minutes and then left at room temperature until the solution became yellowish. Solid sodium bicarbonate (0.028 g, 0.33 mmol) was added, followed by the addition of solid NVOC-Cl (0.091 mg, 0.33 mmol). The reaction mixture was again sparged with argon and stirred at RT for another 12 h. The organic layer was separated from the aqueous layer. The aqueous layer was washed three times with ethyl acetate. The combined organic layer was dried with sodium sulfate, evaporated and then purified by silica gel column using 60% EtOAc/hexanes. Yield=0.022 g (29%). $^1$H NMR: 7.71 (s, 1H), 7.01 (s, 1H), 7.00 (s, 1H), 6.98 (s, 1H), 6.36 (s, 1H), 6.35 (s, 1H), 5.71 (s, 2H), 4.21-4.12 (m, 6H), 3.93 (s, 3H), 3.80 (s, 3H), 3.33-3.23 (m, 8H), 2.36 (t, 2H, J=7.09 Hz), 1.91 (p, 2H, J=7.31 Hz), 1.26 (t, 3H, J=7.13 Hz), 1.14 (t, 3H, J=7.02 Hz). $^{13}$C NMR: 173.2, 153.9, 153.2, 147.9, 145.7, 145.6, 139.4, 133.4, 128.6, 117.8, 117.5, 112.7, 112.5, 109.3, 108.3, 108.0, 99.9, 99.5, 65.0, 60.8, 56.7, 56.4, 47.1, 45.9, 45.2, 31.7, 21.6, 14.5, 10.6. ES-HRMS [M+H]$^+$ 679.2591. Calcd for (C$_{34}$H$_{39}$N$_4$O$_{11}$): 679.2615.

Synthesis of NVOC caged oxazine dye, NHS ester (55): Compound 53 (0.02 g, 0.02 mmol) was refluxed in acetone-water (0.5 mL+0.25 mL) in the presence of 2.5 M HCl (0.015 mL) for 3 h. During this period the ethyl ester was hydrolyzed to the acid 54. The free acid was used to make the corresponding NHS ester without further purification. The free acid was dissolved in dichloromethane (3 ml) followed by the addition of N-hydroxysuccinimide (0.0054 g, 0.047 mmol) and DIC (0.008 ml, 0.047 mmol). The reaction mixture was heated at 45° C. for 3 h. The solvent was evaporated and purified by flash chromatography using 60/40 (v/v) ethyl acetate-hexane. Yield=6.2 mg. $^1$H NMR: 7.71 (s, 1H), 7.01 (s, 1H), 6.99 (s, 1H), 6.97 (s, 1H), 6.36 (s, 1H), 6.33 (s, 1H), 5.71 (s, 2H), 4.18 (t, 4H, J=4.1 Hz), 3.92 (s, 3H), 3.80 (s, 3H), 3.34-3.24 (m, 6H), 2.85 (s, 4H), 2.69 (t, 2H, J=7.0 Hz), 2.04 (p, 2H, J=7.6 Hz), 1.48 (t, 2H, J=6.4 Hz), 1.13 (t, 3H, J=7.0 Hz). ES-HRMS [M+H]$^+$ 748.2483. Calcd for (C$_{36}$H$_{38}$N$_5$O$_{13}$): 748.2466. ES-HRMS of the free acid: [M]$^+$ 650.2200, Calcd for (C$_{32}$H$_{34}$N$_4$O$_{11}$): 650.2224.

OTHER EMBODIMENTS

A number of embodiments have been described. Nevertheless, it will be understood that various modifications may be made without departing from the spirit and scope of the invention. Other embodiments are within the scope of the following claims.

What I claim is:

1. A compound represented by Structure VI:

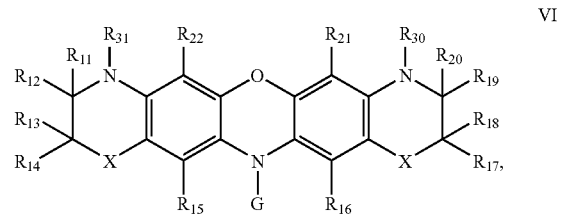

wherein
X is O, S, NH, or CR$_{23}$R$_{24}$,
R$_{30}$ and R$_{31}$ are each independently H, alkyl, alkenyl, alkaryl, aryl, a bis-arsenical spirolactam group, a NHS ester group, a maleimide group, or an iodoacetamide group, each of alkyl, alkenyl, alkynyl, and aryl comprising up to 36 carbon atoms,
R$_{11}$-R$_{24}$ are each independently H, F, Cl, Br, I, OH, alkyl, alkenyl, alkynyl, or aryl, each of alkyl, alkenyl, alkynyl, and aryl comprising up to 36 carbon atoms, and
G is selected from the group consisting of

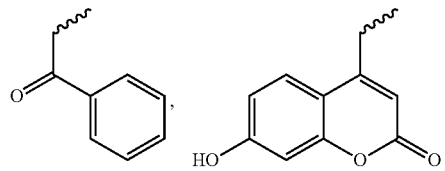

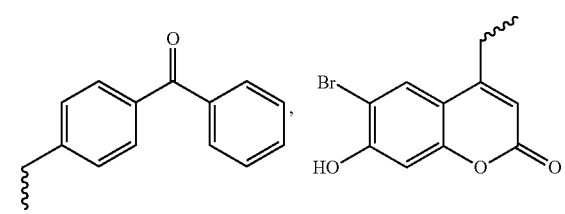

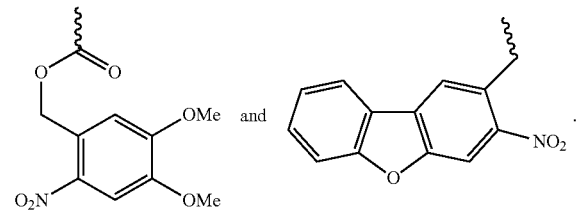

2. The compound of claim 1, wherein one of R$_{30}$ or R$_{31}$ is a bis-arsenical spirolactam group.

3. The compound of claim 2, wherein the bis-arsenical spirolactam group is represented by:

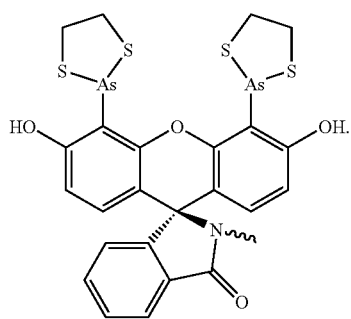

4. The compound of claim 1, wherein one of $R_{30}$ or $R_{31}$ is a NHS ester group, a maleimide group or an iodoacetamide group.

5. The compound of claim 1, wherein the compound after being irradiated with electromagnetic radiation having a wavelength from about 350 nm to about 405 nm, emits a fluorescence in the near-IR region.

6. The compound of claim 1, wherein the compound after being irradiated with electromagnetic radiation having a wavelength from about 350 nm to about 405 nm, emits a fluorescence having a wavelength from about 600 nm to about 900 nm.

7. A compound represented by:

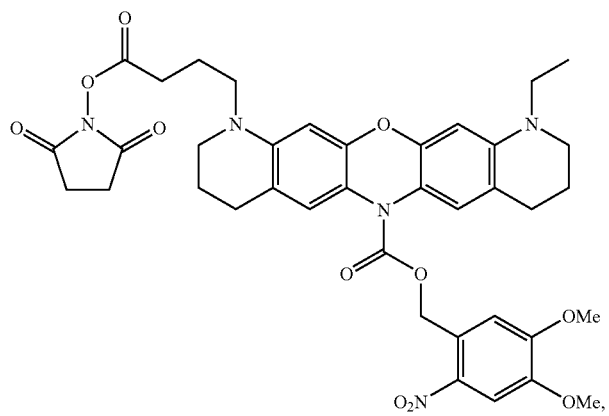

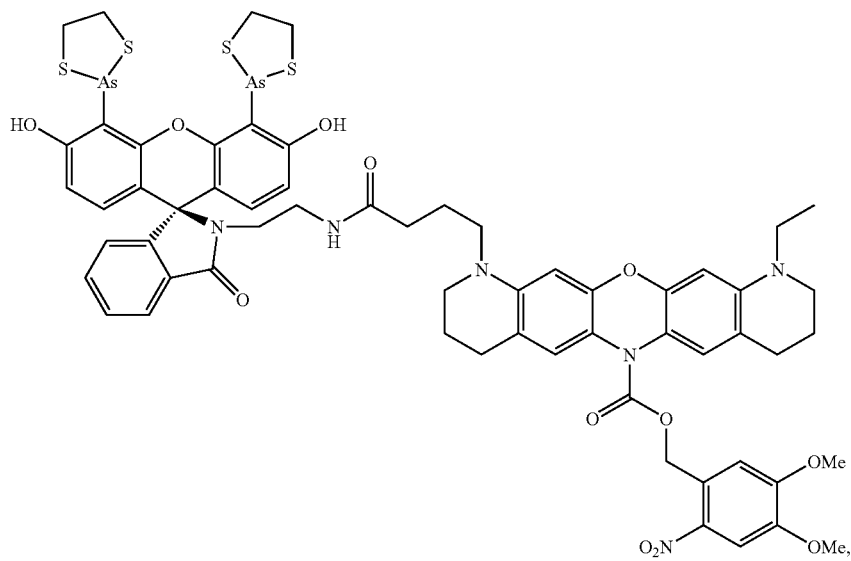

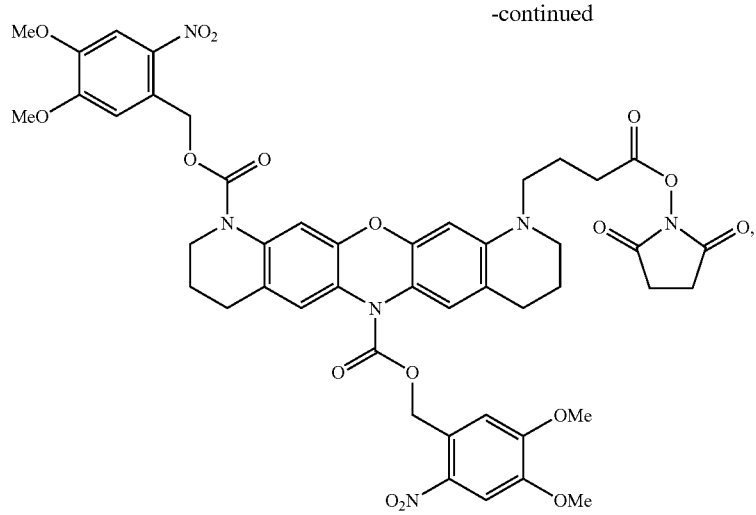

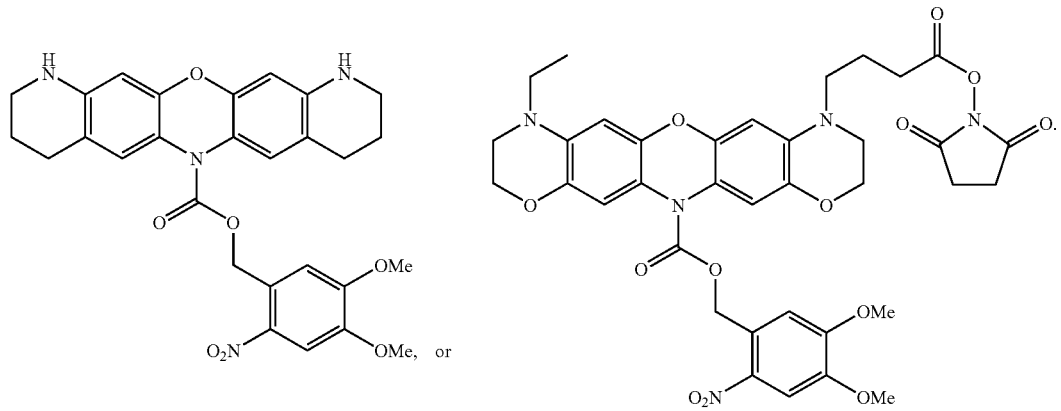

8. A composition comprising a compound of claim 4, wherein the compound is conjugated to a protein.

9. A method of imaging a cell, the method comprising:
providing a cell;
contacting the cell with a compound of claim 1;
irradiating the compound in the presence of an oxidant to provide an active compound; and
detecting emission from the active compound, thereby imaging the cell.

10. The method of imaging of claim 9, wherein the cell is in an animal.

11. The method of claim 9, wherein the oxidant is oxygen.

* * * * *

UNITED STATES PATENT AND TRADEMARK OFFICE
CERTIFICATE OF CORRECTION

PATENT NO. : 8,679,776 B2  
APPLICATION NO. : 12/677962  
DATED : March 25, 2014  
INVENTOR(S) : Stephen C. Miller Page 1 of 1

It is certified that error appears in the above-identified patent and that said Letters Patent is hereby corrected as shown below:

TITLE PAGE, (56) References Cited, OTHER PUBLICATIONS, column 2, line 6, delete "Orgnaic" and insert -- Organic --.

TITLE PAGE, (56) References Cited, OTHER PUBLICATIONS, column 2, line 8, delete "Biotechology" and insert -- Biotechnology --.

Signed and Sealed this
Sixteenth Day of September, 2014

Michelle K. Lee
*Deputy Director of the United States Patent and Trademark Office*